(12) United States Patent
Lueck

(10) Patent No.: US 6,556,930 B1
(45) Date of Patent: Apr. 29, 2003

(54) FLUID TREATMENT APPARATUS

(75) Inventor: Stanley R. Lueck, Farmington, NM (US)

(73) Assignee: RODI Systems Corp., Aztec, NM (US)

( * ) Notice: Subject to any disclaimer, the term of this patent is extended or adjusted under 35 U.S.C. 154(b) by 0 days.

(21) Appl. No.: 09/336,184

(22) Filed: Jun. 18, 1999

Related U.S. Application Data

(60) Provisional application No. 60/089,861, filed on Jun. 19, 1998.

(51) Int. Cl.[7] .............................. G01F 23/00; G01F 1/00
(52) U.S. Cl. ......................... 702/50; 700/266; 700/267; 700/271; 210/614
(58) Field of Search ........................... 702/50; 700/2–3, 700/47, 9, 83, 266, 267, 271; 210/614, 739, 741–746, 96.1

(56) References Cited

U.S. PATENT DOCUMENTS

| | | | |
|---|---|---|---|
| 4,083,777 A | | 4/1978 | Hutchisson |
| 4,498,982 A | | 2/1985 | Skinner |
| 4,514,304 A | | 4/1985 | Miyaki et al. |
| 4,583,170 A | | 4/1986 | Carlin et al. |
| 4,587,518 A | | 5/1986 | King |
| 4,717,425 A | | 1/1988 | Lefebvre |
| 4,830,757 A | * | 5/1989 | Lynch et al. ................. 210/742 |
| 4,849,098 A | | 7/1989 | Wilcock et al. |
| 5,091,863 A | | 2/1992 | Hungerford et al. |
| 5,172,332 A | | 12/1992 | Hungerford et al. |
| 5,299,141 A | | 3/1994 | Hungerford et al. |
| 5,422,014 A | | 6/1995 | Allen et al. |
| 5,578,213 A | | 11/1996 | Miller et al. |
| 5,633,809 A | | 5/1997 | Wissenbach et al. |
| 5,646,863 A | | 7/1997 | Morton |
| 5,647,973 A | | 7/1997 | Desaulniers |
| 5,647,986 A | * | 7/1997 | Nawathe et al. ............ 210/608 |
| 5,687,091 A | * | 11/1997 | Maung et al. ............... 700/266 |
| 5,696,696 A | | 12/1997 | Gunther et al. |
| 5,744,072 A | | 4/1998 | Karliner |
| 5,779,911 A | | 7/1998 | Haug et al. |
| 5,923,571 A | | 7/1999 | Gunther et al. |
| 6,035,240 A | * | 3/2000 | Moorehead et al. ........... 700/2 |
| 6,074,551 A | | 6/2000 | Jones et al. |

OTHER PUBLICATIONS

Anderson, C., ed., *RODI News*, Aug., 1998, pp. 1–3, Creative Geckos, Farmington, New Mexico.
*AquaLynx™ 400, General Operating Manual*, Oct., 1998, RODI Systems Corp., Aztec, New Mexico.
*AquaLynx™ 400 Hardware Manual Version 1.3*, Feb., 1999, RODI Systems Corp., Aztec, New Mexico.
*Technical Bulletin, AquaLynx™ vs. PLCs*, Oct., 1998, RODI Systems Corp., Aztec, New Mexico.

* cited by examiner

*Primary Examiner*—John Barlow
*Assistant Examiner*—Hien Vo
(74) *Attorney, Agent, or Firm*—Andrea L. Mays; Jeffrey D. Myers

(57) ABSTRACT

A fluid treatment apparatus (100) and method having a variety of interchangeable input/output cards (10) capable of communicating with a variety of parameters including analytical parameters. A programmable central processing unit (124), input/output cards (10), data bus (30), display (102), and keypad (104) are integrated into a single integrated apparatus (100). Analytical parameters are received directly by the appropriate input/output cards for direct communication with the central processing unit (124). The central processing unit also outputs control parameters through the input/output cards.

5 Claims, 21 Drawing Sheets

FLUID TREATMENT APPARATUS

CROSS-REFERENCE TO RELATED APPLICATIONS

This application claims the benefit of the filing of U.S. Provisional Patent Application Ser. No. 60/089,861 entitled AQUALYNX WATER TREATMENT APPARATUS, filed on Jun. 19, 1998, and the specification thereof is incorporated herein by reference.

BACKGROUND OF THE INVENTION

1. Field of the Invention (Technical Field)

The present invention relates to the field of fluid monitoring and treatment apparatuses.

2. Background Art

Many different instruments are required to measure the parameters of wastewater, process water, or other fluid being sampled. Maintaining these individual components and tracking the data from these individual components is cumbersome. For example, samplers, flow meters, pH meters, temperature gauges, conductivity and ORP meters, etc., are all used to monitor and track the quality of wastewater, process water, or other fluid being sampled. In fact, most water treatment monitoring systems today comprise an assortment of individual meters and gauges. These individual components are not integrated.

Currently, microprocessor-based control systems are being used in modern industrial processes, including water treatment applications and programmable logic controllers (PLCs) are microprocessor-based. Programmable logic controllers were designed to be a microprocessor-based replacements for hardwired relay logic historically used in industrial control systems. PLCs are programmed to simulate the same type of control that could be accomplished by sets of relays and timers. This is referred to as logic control. Logic control allows certain specific actions to occur based upon other actions or conditions. PLCs have the ability to quickly scan inputs and control outputs based upon the condition of the inputs. However, most PLCs do not have any provisions for storing data (referred to as data logging) or for displaying data on a screen without an additional operator interface.

PLCs also do not have the ability to obtain data directly from water treatment sensors such as pH, ORP, conductivity, etc. This means that an additional meter or transmitter has to be installed between the PLC and the appropriate sensor. A discrete signal is often sent from a relay output on a meter to a discrete input on the PLC. Alternatively, an analog signal may be sent from the meter to an analog input on the PLC. Use of meters in addition to the PLC means additional expense, additional wiring, and additional programming since the meter will have to be programmed for alarm set points and alarm deadband. In summary, current PLCs are used primarily for control. They tend to be difficult if not impossible to use for calculating, manipulating, displaying or storing data. They cannot be used to obtain input directly from most water treatment sensors.

In conventional monitoring systems, it is common to have a number of separate meters monitoring the analytical parameters listed above. Each of these meters may then produce an analog output, which is recorded by some type of control device, such as a PLC. Many PLCs are designed having interchangeable input/output modules. These modules plug into a "rack" or a piece of hardware with multiple connections to some type of data bus, much like the ISA slots in a personal computer. However, in the case of analytical parameters such as pH, oxidation reduction potential (ORP), conductivity, dissolved oxygen, turbidity, corrosion rate, ion specific, etc., conventional systems monitor these parameters with separate discrete instruments. These instruments then send a signal, usually some type of analog signal, to a standard input module on the PLC. Presently available systems do not have input/output modules for analytical parameters available for standard PLCs.

With a conventional PLC, the monitoring and control system is configured by selecting the assorted meters necessary to monitor the parameters of interest. These are hardwired to the PLC and both the PLC and the meters have to be programmed. In the case of the present invention, configuration is done via software rather than hardwiring, and input/output modules are used to monitor and control analytical parameters as well as other parameters. The present invention also allows the user to log data as well as display data.

Patents which disclose devices designed to combine the different conductivity meters, pH meters, ORP meters, flow meters, etc. but unlike the present invention include U.S. Pat. No. 5,091,863, to Hungerford, et al., entitled Automatic Fluid Sampling and Flow Measuring Apparatus and Method, which discloses a device to monitor sewer flows and which is to be mounted inside a manhole. U.S. Pat. No. 5,172,332, to Hungerford, et al., entitled Automatic Fluid Sampling and Monitoring Apparatus and Method, is essentially the same device as that in U.S. Pat. No. 5,091,863 but includes broader program storage memory and data storage memory. U.S. Pat. No. 5,299,141, to Hungerford, et al., entitled Automatic Fluid Monitoring and Sampling Apparatus and Method, again discloses the same device as in the prior two patents but includes a photoelectric type sensor. U.S. Pat. No. 5,633,809, to Wissenbach, et al., entitled Multi-Function Flow Monitoring Apparatus with Area Velocity Sensor Capability, again discloses a similar device to the prior three patents but includes input/output points. However, these are fixed. Additional analog inputs and discrete outputs cannot be added. All of these devices are to be used in monitoring sewer pipes and are mounted in manholes, and their primary purpose is for flow measurement.

Unlike the aforementioned devices, the present invention is reprogrammable even after the unit has been installed. The present invention is designed to be programmed for each application, including logic control functions. It can be used for any type of fluid monitoring and control, not just wastewater. The aforementioned parameters can all be monitored directly from the sensor with the various input/output cards without any additional instrumentation. The input/output cards are interchangeable and selectable by the user and can be interfaced directly to the data bus from the various instruments. The applications for this type of input/output card configuration are endless. Analytical process parameters have not been directly monitored by devices in the prior art. Because it is compact and flexible, the present invention can be mounted on a control panel with standard bracketing. This unique apparatus can be used to monitor streams in industrial settings as well as in the field.

SUMMARY OF THE INVENTION
(DISCLOSURE OF THE INVENTION)

The present invention is an integrated apparatus for monitoring and controlling fluid treatment having a central processing unit to manipulate and control data and at least one interchangeable input/output card for communication with sensor inputs and the central processing unit. The apparatus optionally has a keypad for the user to communicate directly with the central processing unit. Various interchangeable input/output cards are available for the fluid treatment apparatus. These cards include analog/pulse input cards, analog output cards, digital input/output cards, conductivity input cards, pH/ORP input cards, water treatment combination cards, temperature input cards, combination conductivity and resistivity input cards, pH input cards, ORP input cards, dissolved oxygen input cards, corrosion rate input cards, turbidity input cards, particle counting input cards, modem cards, printer interface cards, memory cards, and serial communication cards. The fluid treatment apparatus can have a data bus for communicating between the input/output cards and the central processing unit. A serial port is available for communicating with external devices. The fluid treatment apparatus is compact and integrated and can be mounted on a control panel.

The software upon which the CPU operates can perform a variety of calculations, including but not limited to calculating differential pressure, flow recovery, energy consumption, chemical usage, total operating time, total volume processed, salt rejection, temperature differential, heat loss, and normalized data. The software is also capable of setting alarms and logging alarm events. By using the software, the user can label inputs, establish ranges for inputs, establish alarm set points for inputs, designate alarm relays, set analog output ranges, calculate results, store data, display real time data, display stored data, and perform data transfer. The fluid treatment apparatus also has internal memory to store data. A display is provided for viewing data. Preferably the display is an LCD display.

At least one of the interchangeable input/output cards is capable of directly communicating with analytical sensors. Preferably the apparatus can communicate directly with conductivity sensors, pH sensors, ORP sensors, temperature sensors, dissolved oxygen sensors, turbidity sensors, ion specific sensors, and flow sensors.

Preferably PC-compatible software is used to program the central processing unit. Passive backplane architecture is used in the apparatus and card guides are used for retaining the interchangeable input/output cards.

The apparatus has applications in several technologies. Reverse osmosis operations can be monitored and controlled with the apparatus with at least one reverse osmosis vessel, at least one analytical sensor, and at least one pressure pump in communication with each other and in direct communication with the apparatus. A plurality of apparatuses can also be networked and in communication with an industrial personal computer, sensors, and control devices, such as pumps and valves, for monitoring and controlling a plurality of fluid treatment applications.

Cooling towers can be monitored and controlled with the apparatus with the apparatus in communication with the tower, chemical injection pump, and valves necessary for controlling the tower.

The unique configuration of the input/output cards capable of communicating directly with analytical sensors and in turn communicating those inputs to the central processing unit has applications in other technologies. Analytical parameters can be monitored with the central processing unit, data bus, and at least one input/output card to receive the analytical parameters and communicate them to the central processing unit.

A method for controlling and monitoring fluid treatment involves manipulating fluid treatment data with the central processing unit of the apparatus, controlling fluid treatment with the central processing unit, communicating with sensor inputs with the interchangeable input/output cards, and outputting control parameters with the interchangeable input/output cards. The user can optionally communicate with the central processing unit via a keypad. The input/output cards can communicate with the central processing unit via a data bus. Data can be communicated with external devices, such as printers, computers and the like, by communication through an optional serial port. Calculating fluid treatment parameters is accomplished by programming the central processing unit. The central processing unit can perform a number of calculations including differential pressure, flow recovery, energy consumption, chemical usage, operating time, volume processed, salt rejection, temperature differential, heat loss, and normalized data. It can also set alarms and log alarm events. By programming the central processing unit, the user can label inputs, establish ranges for inputs, designate alarm relays, set analog output ranges, perform calculations, store data, display stored data, display real-time data, and perform data transfer. The user can further control and monitor applications by displaying data on the screen of the apparatus and viewing such data. The user can also select and interchange the various input/output cards to tailor the apparatus to the desired application.

A primary object of the present invention is to provide the ability to directly receive analytical parameters.

Another object of the present invention is to monitor and control a variety of fluid treatment parameters with one integrated programmable apparatus.

Yet another object of the present invention is to monitor and control fluid treatment parameters from a central location mounted on a single control panel.

Still another object of the present invention is to provide an integrated apparatus for monitoring and controlling fluid treatment parameters that is easily programmed and simple to operate.

A primary advantage of the present invention is that individual meters and gauges are not necessary to monitor and control fluid treatment parameters.

Other objects, advantages and novel features, and further scope of applicability of the present invention will be set forth in part in the detailed description to follow, taking in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

Figure 1:
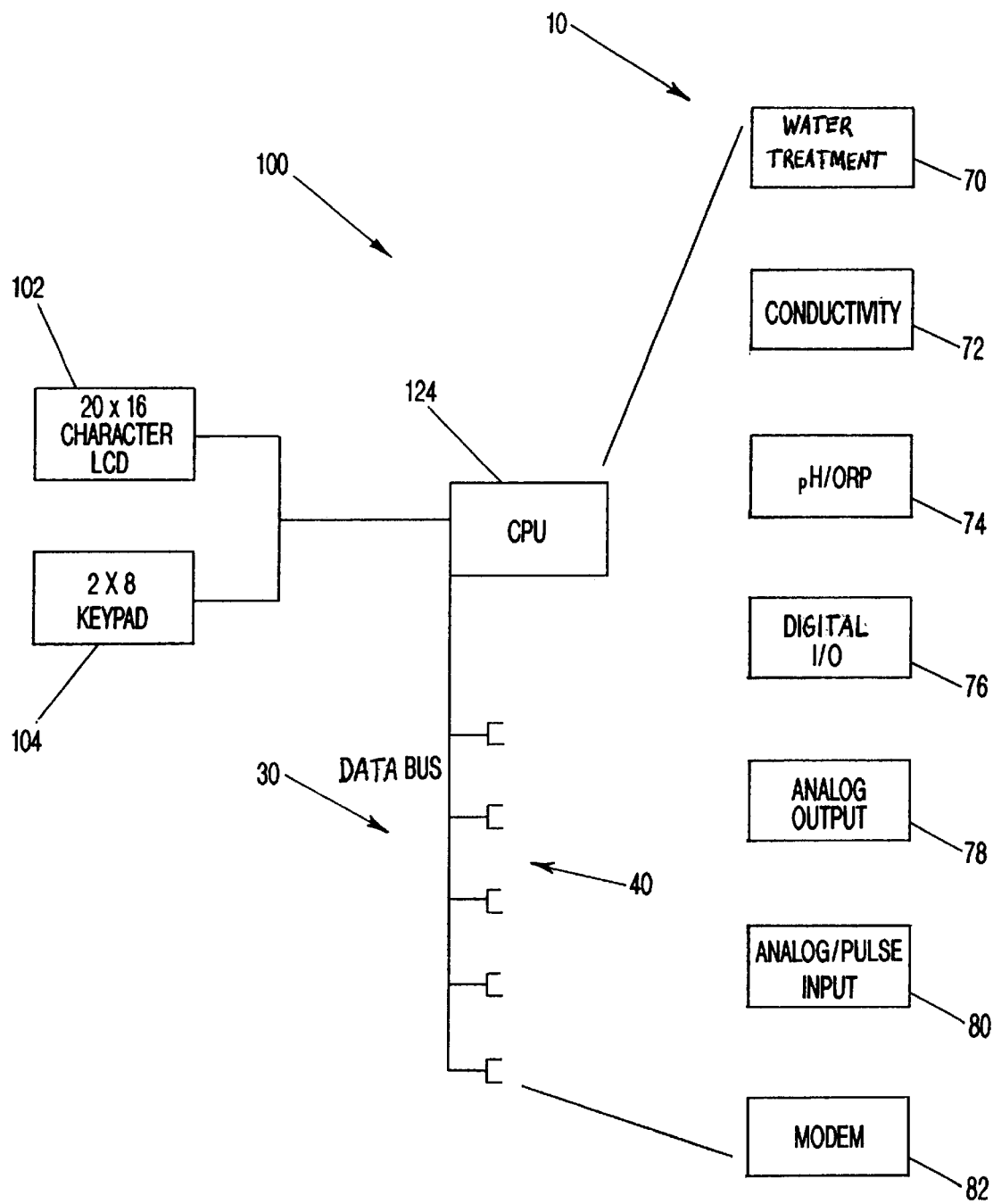
FIG. 1 is a block diagram of the preferred embodiment of the invention.

DESCRIPTION OF THE PREFERRED EMBODIMENTS (BEST MODES FOR CARRYING OUT THE INVENTION)

The present invention is a programmable, integrated compact data acquisition, monitoring, and control system designed for fluid treatment applications. It is capable of monitoring a variety of inputs, for example pressure, conductivity, pH, ORP, temperature, and flow and is designed to replace the usual assortment of meters and gauges making up most fluid treatment monitoring systems. Since it is an integrated monitor, all of the operating parameters are examined by the same instrument. The apparatus can also calculate values such as differential pressure, flow recovery, energy consumption, chemical usage, total operating time, total volume processed, salt rejection, temperature differential, heat loss, and normalized data with the CPU. Alarm set points can be entered for both primary and calculated parameters and alarm events are logged to an internal alarm log. The present invention can also log operating data, transmit data via modem, or print data on an optional printer.

In the preferred embodiment, the fluid treatment apparatus is equipped with a serial port which may be configured as either RS-232 or RS485. This allows the apparatus to communicate with a number of third-party devices such as personal computers, PLCs, printers, modems, and distributed control systems. The apparatus comes with appropriate software for downloading data via direct connection or modem. Preferably Windows 95 or comparable software is used. The apparatus is ideal for a number of fluid and water treatment applications, including cooling towers, boilers, reverse osmosis units, ion exchange units, reverse osmosis and ion exchange pretreatment systems, and wastewater treatment.

Passive backplane architecture provides versatility to the apparatus. The unit houses a central microprocessor connected to a passive backplane containing a number of expansion slots. These slots may be equipped with one or more of a variety of input/output cards available for specific types of input and output. By selecting the appropriate display/CPU unit along with the appropriate input/output card or cards, the end user can configure a monitoring system for a specific application. Many different input/output cards are available to choose from.

Example input/output cards include the following. A combination input card preferably receives inputs from two conductivity cells, two temperature sensors for conductivity temperature compensation, four flow sensors, and four auxiliary analog inputs from four to twenty milliamps. A conductivity input card preferably receives inputs from two conductivity cells and two temperature sensors for temperature compensation. A pH/ORP card preferably receives input from either two pH probes, two ORP probes, or a combination of the two. It also receives inputs from two temperature sensors for pH temperature compensation. The digital input/output card is preferably equipped with eight optically isolated digital inputs capable of receiving signals up to 48 volts AC or DC. It is also equipped with eight single pole single throw relays able to withstand three amperes at 120 volts. The analog/flow input card is a general purpose card capable of accepting eight four to twenty milliamp analog inputs (single-ended, non-isolated) and six flow inputs. The flow inputs are configured to accept open collector outputs from Hall effect type flow sensors. The analog output card is preferably equipped with four non-isolated, single-ended, analog four to twenty milliamp outputs. The parallel printer interface card allows the apparatus to print data to any printer equipped with a parallel interface. A serial communication card can also be programmed for specific communication protocols such as Modbus, DeviceNet, Profibus, and others. A temperature card is available for a thermocouple, RTD resistor, and thermistor. An individual pH card is also available. The apparatus also accommodates a conductivity and resistivity card. An individual ORP card can be used, as well as a dissolved oxygen card. A corrosion rate card is available and is accomplished by means of linear polarization resistance or other standard means. Turbidity and particle counting cards can also be placed into the apparatus. A modem card allows the apparatus to transmit data via modem when used in conjunction with data transfer software. These are just examples of the many different input/output cards available and comprise only one embodiment of each. Many alternative embodiments for each input/output card would be obvious to those skilled in the art.

Although many features and components can be used to configure the apparatus, the apparatus most preferably uses the following: a NEMA 12-panel mounted enclosure, a Phillips 80C552 microprocessor (22 megahertz), 128K SRAM with lithium backup, a 128K FLASH memory, a Dallas real time clock, an RS-232/RS-485 serial port, a 20 by 16 character LCD display with LED backlight, a 2 by 8 numeric keypad, a five amp and 120/240 volt to 24 volt transformer or 24 volt DC power supply, and software for system configuration and data transfer. Preferably, Windows-based software is used in the apparatus.

The software is used for two purposes. First, it provides a way in which the user can configure the hardware of the apparatus for a specific application. The software also allows the user to label individual inputs, establish ranges and alarm set points for each input, designate alarm relays for various parameters, and set analog output ranges for various parameters. Data transfer software is used for downloading data either by direct serial connection or remotely via modem. Data downloaded from the apparatus may be saved in an ASCII delimited format. This makes it possible to read the data with virtually any spreadsheet program. The apparatus also includes a PCMCIA interface in the preferred embodiment. This hardware allows the apparatus to download data to a standard PCMCIA memory card. Data saved to the card may then be uploaded to any personal computer.

In the preferred embodiment, the entire fluid treatment apparatus is approximately 5.25 inches wide, 5.25 inches high, and 6.25 inches deep. It weighs approximately three pounds. Power consumption for the apparatus is five amps at 24 volts AC or DC. The system can be equipped with a 120/240 volt transformer or 24 volt DC power supply.

The software configuration for the present invention is preferably a Windows-based package. The user loads the software on a standard personal computer and starts designing the system by inputting the parameters to be monitored, including their names, units, scales, and so on. Next, any calculated values are included by typing in the appropriate formula. Alarms are then defined, including high and low set points and alarm deadbands. After the configuration is complete, the information is downloaded to the fluid treatment apparatus via a serial transfer cable. Then the apparatus is ready for use. Frequently changed parameters such as alarm set points and deadbands may be changed directly from the keypad. The central processing unit (CPU) of the apparatus is different from those commonly used in PLCs. The CPU in the fluid treatment apparatus is powerful and equipped with a large amount of memory. This allows the apparatus to store a large amount of data. The software allows the CPU to be programmed in BASIC programming language rather than ladder logic which is used by most PLCs. This means that the apparatus has the ability to easily calculate, store, and otherwise manipulate data.

A simple example of a logic statement might be as follows: "Start the feed pump if the selector switch is in the auto position and if the level switch is in the low position. Start the high pressure pump ten seconds after starting the feed pump." The BASIC source code used to perform this logic control would be as follows:

```
10   XIH 016: XIL 017: OTE 000      REM starts feed pump
11   XIH 000: DLY 000, 010: OTE 002 REM delays start of HP pump
12   GO TO 10
```

These logic instructions are entered during the configuration procedure with the Windows configuration software. Unlike most PLCs, the fluid treatment apparatus serves as its own operator interface. Messages may be programmed into logic portion of the configuration to appear on the screen during operation. Also, the status of all input/output points may be viewed by selecting the appropriate screen from the fluid treatment apparatus main menu. Preset values for counters and timers may be changed directly from the keypad without having to connect to a laptop personal computer or handheld programming unit. Therefore configuration for the apparatus' monitoring and control is done via software rather than through hardwiring. This data can then be processed and stored and transmitted via modem or a serial connection. The entire operation occurs at the fluid treatment apparatus.

The fluid treatment apparatus may be programmed to do any calculations. This allows data to be calculated automatically and in real time, thus lowering manpower requirements and providing up-to-date information. A typical example is the calculation of normalized permeate flow from reverse osmosis units.

The apparatus also stores operating data to internal memory for later retrieval with any personal computer via serial port or modem, or stored to an optional memory card. The memory card may also be used for uploading the system configuration. Furthermore, the fluid treatment apparatus logs all alarm events, which may be viewed directly on the fluid treatment apparatus display. Discrete input/output status may be viewed on the display during operation to facilitate troubleshooting without having to connect a personal computer or handheld programming unit to the controller. The ability to program and display status messages eliminates the use of PLC operator interfaces. The modem input/output card allows communication to personal computers via standard telephone lines. A serial port allows networking via serial communication. As stated previously, the fluid treatment apparatus is capable of directly monitoring a number of fluid treatment analytical process parameters such as conductivity, pH, ORP, temperature, dissolved oxygen, turbidity, ion specific, and flow. It is also capable of monitoring virtually any other parameter via standard four to twenty milliamp analog signals or via discrete signals.

The apparatus is also capable of calculating additional data based upon raw process data. These values, along with raw data, may then be logged for future evaluation. The apparatus can also be used to control process conditions. This may be as simple as opening and closing relay contacts based upon alarm conditions or it may be more elaborate and involve logic control for a particular process. Each fluid treatment apparatus is programmed separately and for a particular application.

Raw operating data is logged into an internal memory location. The logging interval for the data is preferably once every 30 minutes. Due to the large volume of data acquired in the data log, the data is not viewable on the LCD of the apparatus. It can, however, be downloaded by connecting a personal computer to the serial port (either locally or via modem) with the software.

In the preferred embodiment, operation of the apparatus is very simple since it is completely menu driven, with the only exception being sensor calibration. Upon power up, the apparatus will display a main menu from which the operator may choose from a number of screens by pressing the appropriate key on the keypad. Data screens allow the user to observe real time operating data. A settings menu allows changes to parameters such as set points, deadbands, time delays, flow sensor K factors, and conductivity correction factors, analog ranges and scales, and time delays. An access code is entered in order to change settings. K factors must be entered for all flow sensors providing a pulse signal. The K factor is defined as the number of pulses produced by the flow sensor by every gallon that passes through the sensor. The alarm history screen allows the operator to view alarms logged by the fluid treatment apparatus. An output status screen allows the operator to view the status of output relays. The input screen allows the operator to view the status of discrete inputs and internal memory bits. These are just some of the screens and capabilities of the fluid treatment apparatus, all of which are controlled by BASIC software. All parameters are monitored and displayed by one panel-mounted apparatus. This means that a number of calculated values can be continuously monitored, recorded, and displayed, a feature important in monitoring and controlling water treatment systems. A Windows-based configuration application is provided as an alternative embodiment for the fluid treatment apparatus in place of the direct BASIC programming embodiment.

Attention is now turned to the figures. FIG. 1 shows a basic block diagram of one embodiment of fluid treatment apparatus 100. Example input/output cards are shown generally at 10. The input/output cards can be water treatment combination card shown at 70, conductivity card 72, pH/ORP card 74, digital input/output card 76, analog output card 78, analog/pulse input card 80, and, modem card 82. CPU 124 communicates with input/output cards 10 via I/O card data bus 30. Bus connectors are shown generally at 40. CPU 124 communicates with a 20 by 16 character LCD display 102 and 2 by 8 keypad 104. Of course, these dimensions are variable, and FIG. 1 only shows a preferred embodiment of the present invention.

Figure 2:
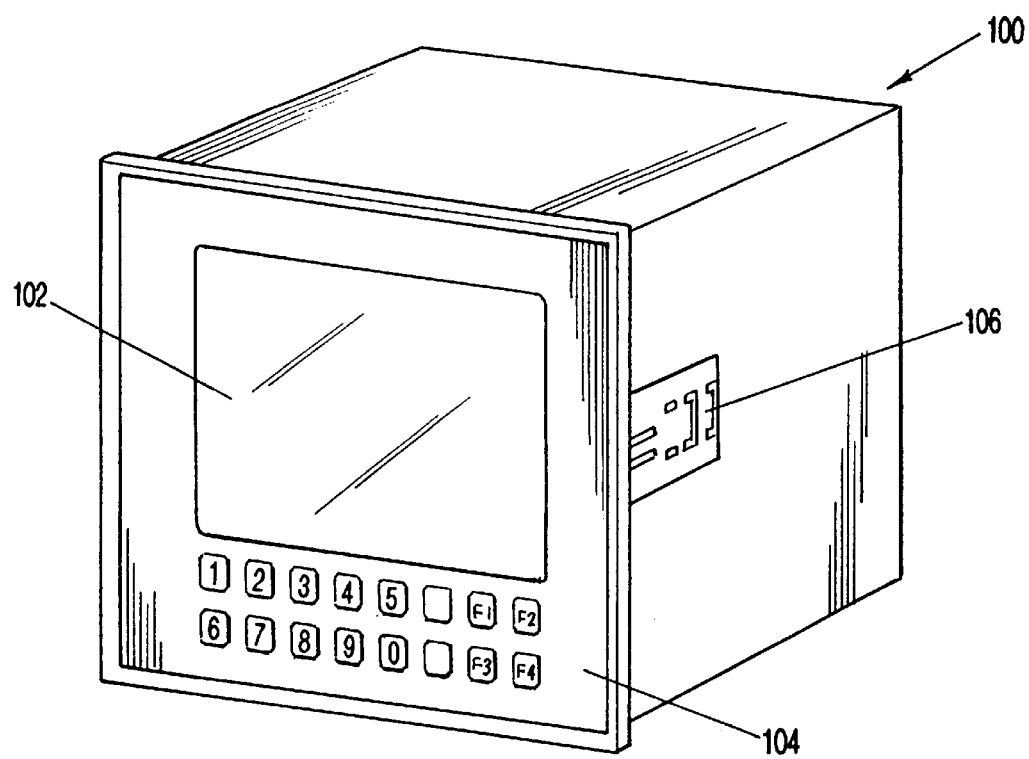
FIG. 2 is a perspective frontal view of the display module of the present invention.

FIG. 2 is a perspective view of fluid treatment apparatus 100. Display 102 displays various parameters and directs the user through various menus and user input operations. Keypad 104 is used to program and operate the apparatus. Attachment points 106 allow clamps to be attached for panel mounting.

Figure 3:
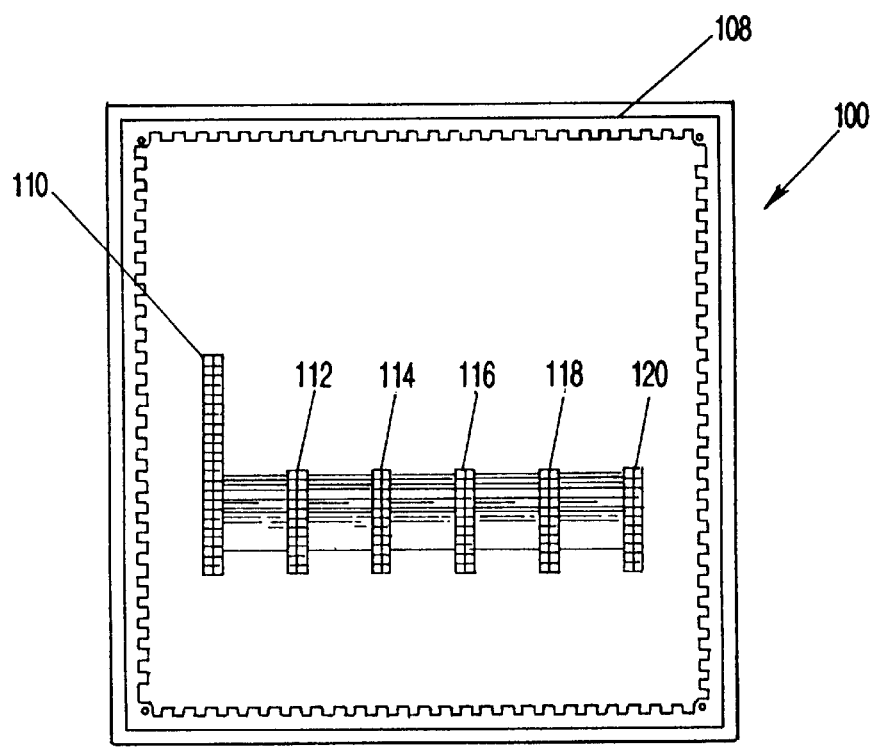
FIG. 3 is a rear view of the display module showing input/output connectors of the present invention.

FIG. 3 shows a rear view of fluid treatment apparatus 100. The backplane in fluid treatment apparatus 100 is equipped with six ports which consist of CPU connector port 110, and input/output card connector ports 112, 114, 116, 118, and 120. CPU connector port 110 is always occupied by the CPU card. Card guides shown generally at 108 provide guides for sliding the CPU and various input/output cards into the rear of fluid treatment apparatus 100.

Figure 4:
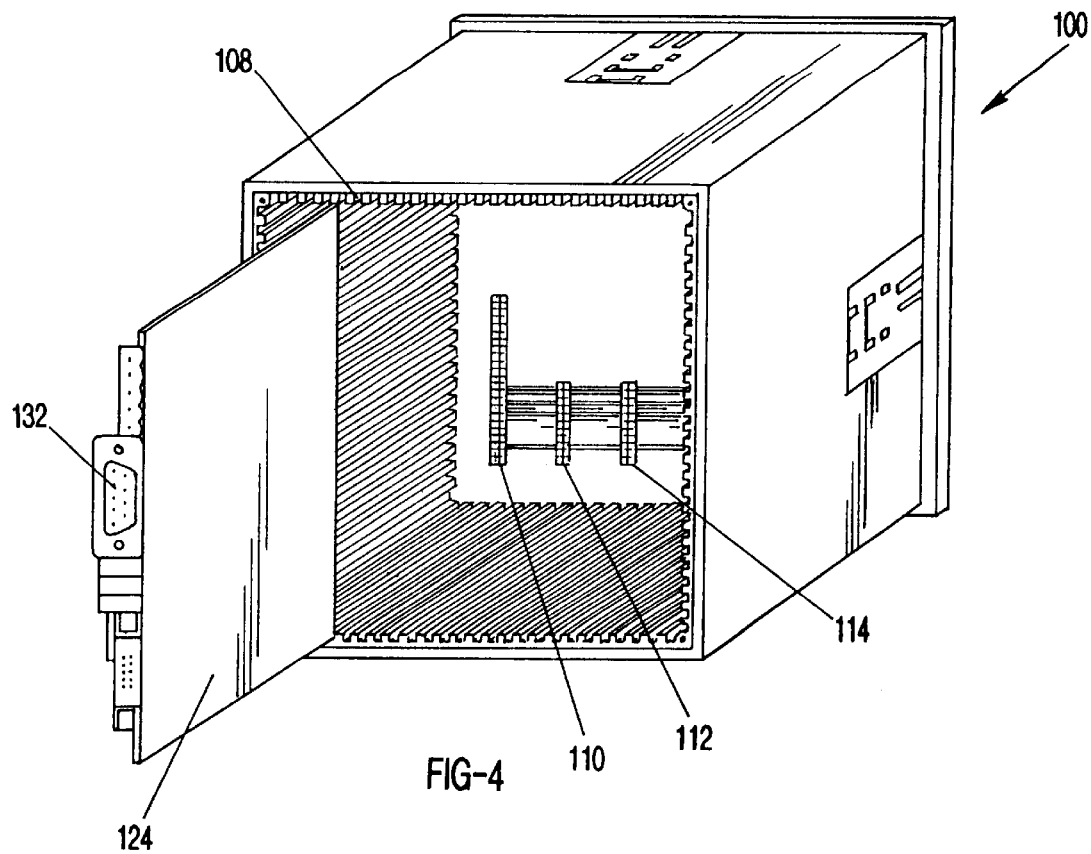
FIG. 4 is a perspective rear view showing the card guides of the present invention.
Figure 5:
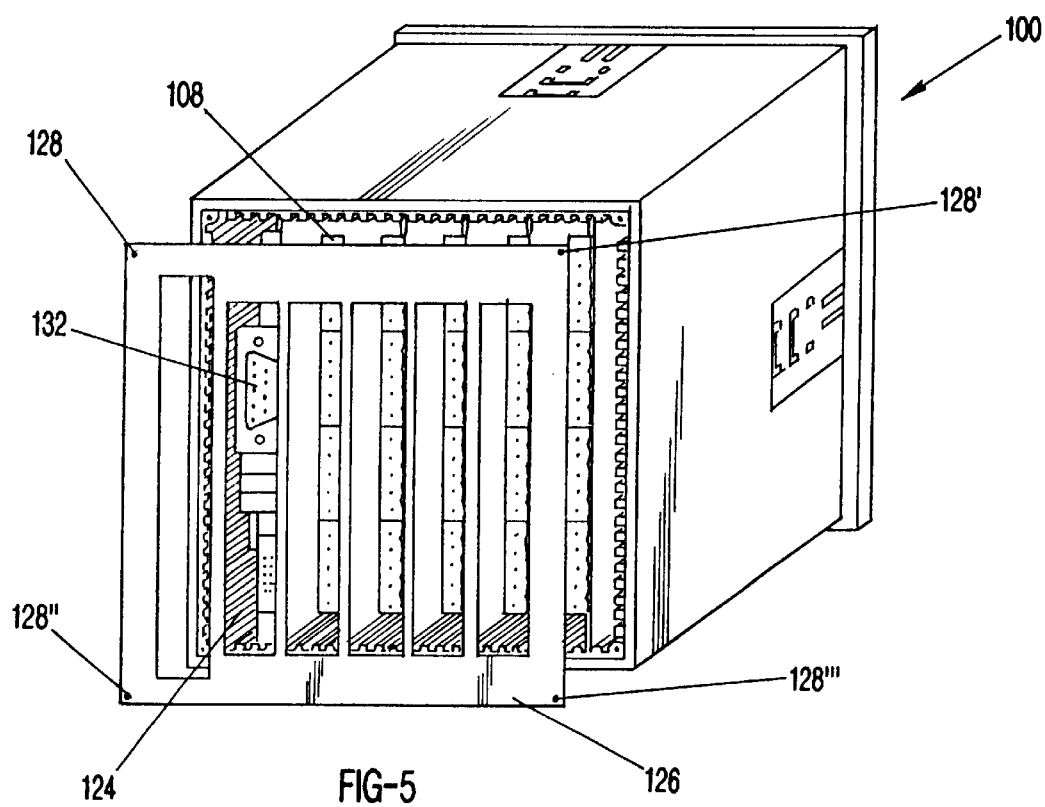
FIG. 5 is a perspective rear view of the display module and back plate of the present invention.

FIG. 4 shows fluid treatment apparatus 100 and CPU card 124 as it is slid into the rear of fluid treatment apparatus 100 via one of card guides 108. Serial port 132 provides communication with external devices. As shown in FIG. 5, once the CPU and selected input/output cards are placed in the rear of fluid treatment apparatus 100, back plate 126 is screwed via screws 130, 130', 130", and 130'" and screw holes 128, 128', 128", and 128'" onto the rear of fluid treatment apparatus 100.

Figure 6:
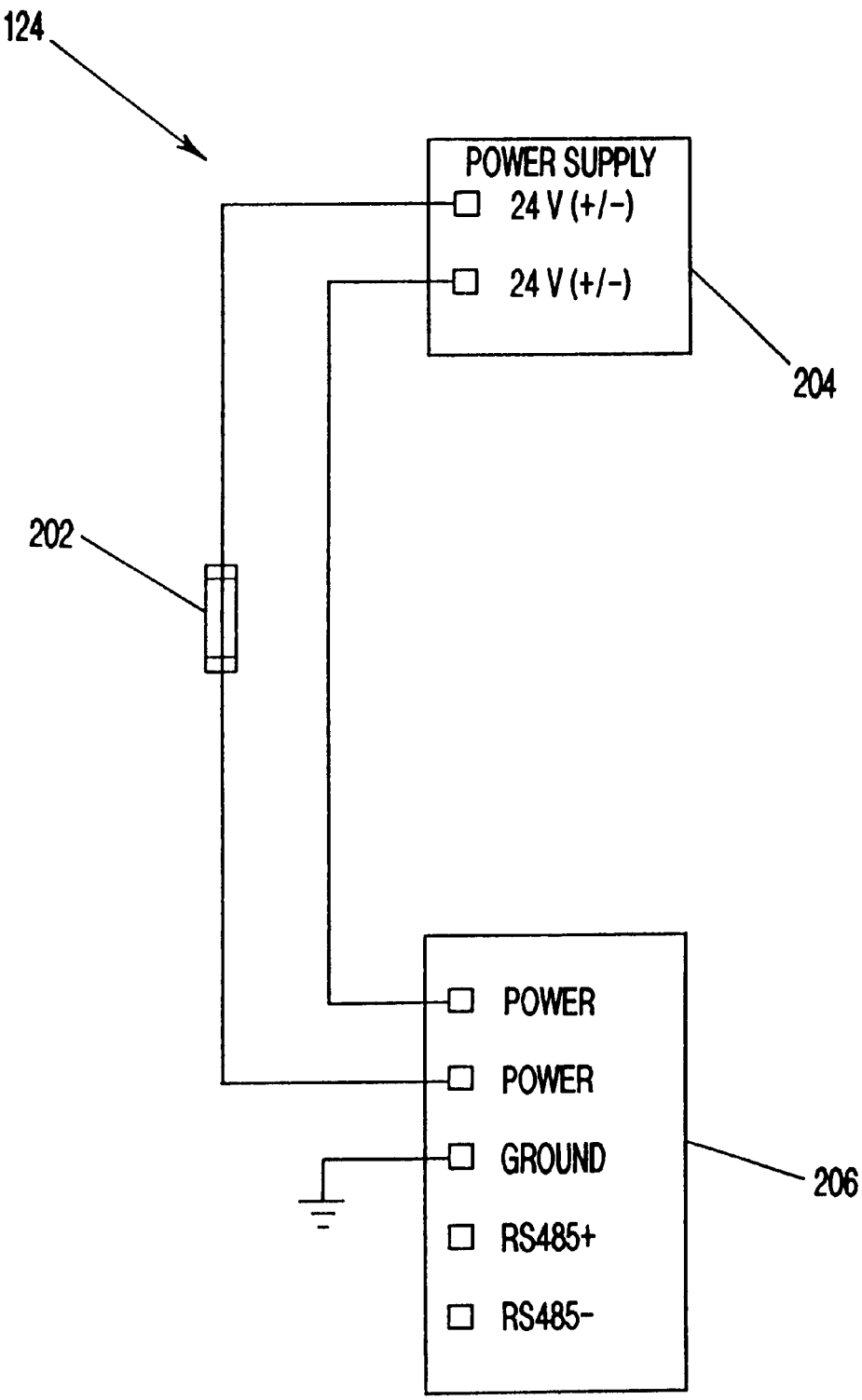
FIG. 6 is a schematic diagram of the terminal connections on the main central processing unit card of the present invention.

FIG. 6 shows the terminal connections on the main CPU card 124 as a schematic block diagram. Power supply 204 provides either 24 volts AC or DC. The two power inputs are bipolar, i.e., positive power may be connected to either of the two terminals. Fuse 202 is used to protect the power connection to CPU card 124. Power, ground, and RS-485 connections are shown generally at 206. CPU card 124 should be properly grounded to earth ground. CPU card 124 serves several functions, including storing and executing the main control program, communicating with the input/output cards via the bus, communicating with external devices via serial port 132, receiving input from keypad 104, and sending output to display 102.

Figure 7:
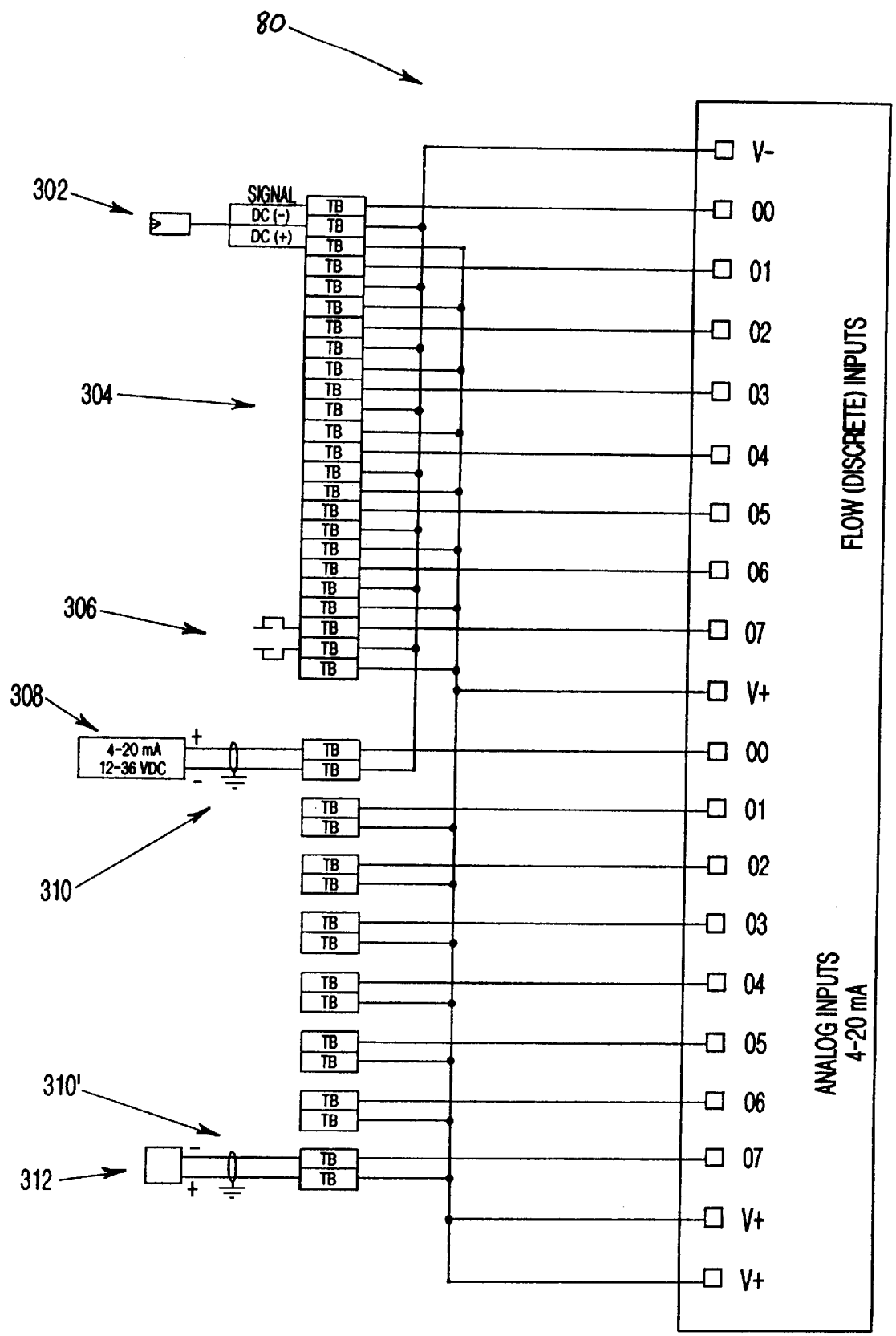
FIG. 7 is a schematic-block diagram of the terminal connections on the analog/flow input card of the present invention.

Analog/flow input card 80 terminal connections are shown as a schematic block diagram in FIG. 7. This card is designed to be used with flow sensors equipped with an open collector, Hall effect output. The analog/flow input card is a general purpose card which allows fluid treatment apparatus 100 to receive input from other devices producing preferably a four to twenty milliamp signal. It also may be used to receive input from devices producing a sinking pulse by means of a Hall effect sensor. In the preferred embodiment of the invention, one fluid treatment apparatus 100 will support up to eight analog/flow input cards. The analog/flow input card has eight single-ended 12-bit inputs at four to twenty milliamps, and eight sinking pulse 12 to 24 volts DC. Power required for the analog/flow input card is either five volts DC or 24 volts DC via the bus connection. Twenty-four volts DC is supplied to two wire transmitters via terminal connectors. This card is programmed using either BASIC or Windows configuration software. Hall effect flow sensors have three lead connections 302, one for positive DC, one for negative DC, and one for the return signal for sinking pulse. Terminal blocks 304, for example, DIN rail style, should be used to connect terminals to field wiring. This allows smaller gauge wire to be used on the terminals. Flow inputs may also be used as discrete inputs 306, such as for hand switches and float switches. Input 306 is high when connected to the low side of the DC supply, sinking input. Some devices produce their own four to twenty milliamp signal without requiring power from fluid treatment apparatus 100. These devices may be used with the analog/flow input card and connected at 308. However, they must produce an isolated output of sufficient amperage. These devices are interfaced by connecting the positive output of the device to the analog input of the card. The negative side of the device is connected to the V− terminal of the card. Analog devices should be connected to fluid treatment apparatus 100 with shielded cable 310, 310'. The shield of the cable should be grounded but only at one end of the cable. Two wire analog transmitters at four to twenty milliamps may be powered by the 24 volt DC output 312 from the analog/flow input card. The positive side of the transmitter is connected to the V+ terminal of the card. The negative side of the transmitter is connected to the analog input.

Figure 8:
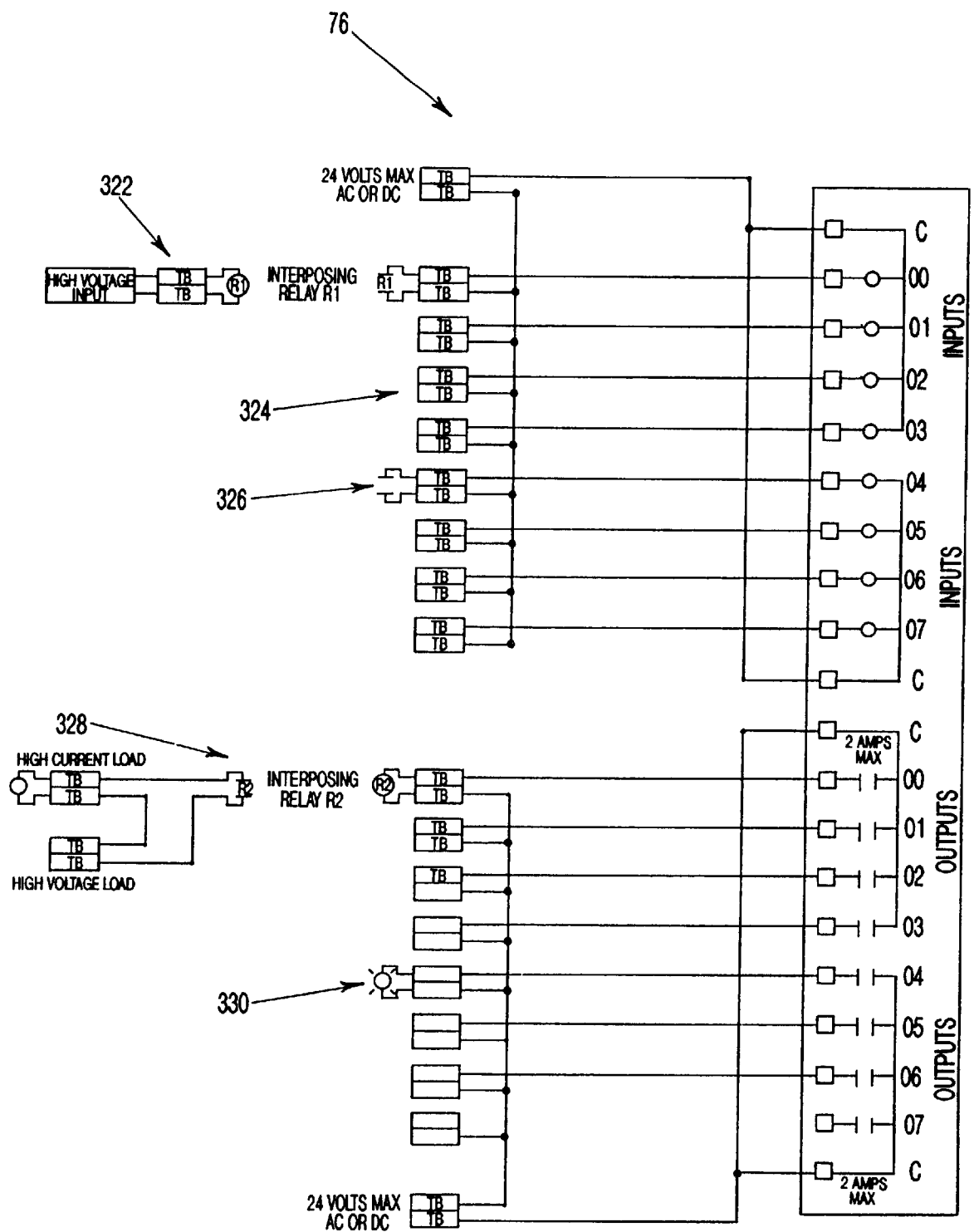
FIG. 8 is a schematic-block diagram of the terminal connections on the digital input/output card of the present invention.

Digital input/output card 76 terminal connections are shown as a schematic block diagram in FIG. 8. Digital input/output card 76 is a general purpose card which allows fluid treatment apparatus 100 to receive discrete inputs from devices such as level switches, hand switches, float switches, push buttons, selector switches, pressure switches, and PLC relay outputs. It is also equipped with relay outputs to control pumps, motors, lights, valves, and other devices. In the preferred embodiment of the invention, one fluid treatment apparatus 100 will support up to eight digital input/output cards. The digital input/output card has eight optically isolated inputs, two groups of four, with one common connection per group. Input voltage is limited to 24 volts AC or DC. The output of digital input/output card 76 is eight SPST (single pole single throw) relays in two groups of four, with one common connection per group. Switched voltage is limited to 24 volts AC or DC, with a maximum current of two amps per common connection. Relay contacts are protected with MOVs. Digital input/output card 76 requires five volts DC, 24 volts DC via the bus connection. Inputs with voltages greater than 24 volts AC or DC must be interfaced through an interposing relay 322 or isolator. Terminal blocks 324, for example, DIN rail style, should be used to connect terminals 324 to field wiring. This allows smaller gauge wire to be used on the terminals 324. Low voltage discrete inputs 326, less than 24 volts AC or DC, may be connected directly to the inputs. Applications that require switching of voltages greater than 24 volts AC or DC or switching of high loads, greater than two amps per output group, must use interposing relays 328. Low voltage, low load outputs may be switched directly by output relays 330. Relays 322, 328 and 330 enable fluid treatment apparatus 100 to control devices such as solenoid valves, motor starters, indicator lights, and alarms. It is apparent that, when properly programmed, fluid treatment apparatus 100 can replace PLCs in most water treatment applications.

Figure 9:
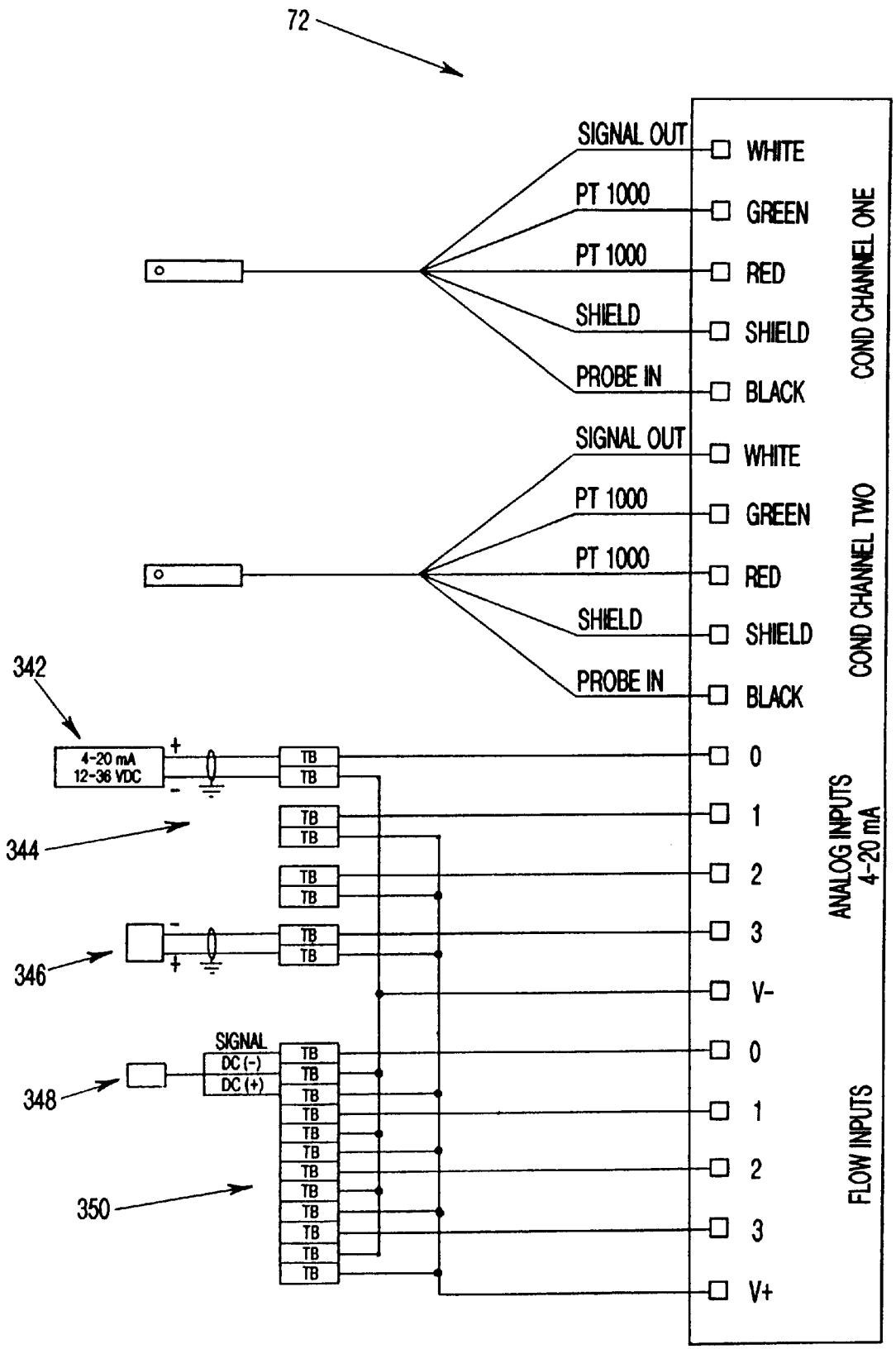
FIG. 9 is a schematic-block diagram of the terminal connections on the conductivity input card of the present invention.

Conductivity input card 72 terminal connections are shown generally in FIG. 9 as a schematic block diagram. Conductivity input card 72 allows fluid treatment apparatus 100 to monitor two standard conductivity cells. The cells are equipped with 1,000 ohm platinum RTD resistors for temperature compensation in the preferred embodiment. It is also able to receive input from four other devices producing a four to twenty milliamp signal 342 and from three devices producing a sinking pulse by means of a Hall effect sensor. In the preferred embodiment, one fluid treatment apparatus 100 will support up to eight conductivity input cards 72 and contains two electrode conductivity cells inputs, two 1,000 ohm platinum RTD resistor sensors, four single-ended 12-bit inputs at four to twenty milliamps, and three sinking pulse inputs at 12 to 24 volts DC. Conductivity input card 72 requires five volts DC or 24 volts DC via the bus connection, and supplies 24 volts DC to two wire transmitters via terminal connectors. Shielded cable 344 is shown to connect analog devices to fluid treatment apparatus 100. Two wire analog transmitters, four to twenty milliamps, may be powered by the 24 volt DC output 346 from conductivity input card 72. Hall effect flow sensors have three lead connections 348, one for DC+, one for DC-, and one for the return signal, sinking pulse. Terminal blocks 350, for example, DIN rail style, should be used to connect the fluid treatment apparatus terminals to field wiring. This allows smaller gauge wire to be used on the terminals. Proper ranges for each conductivity channel are set by dip switches on the card.

Figure 10:
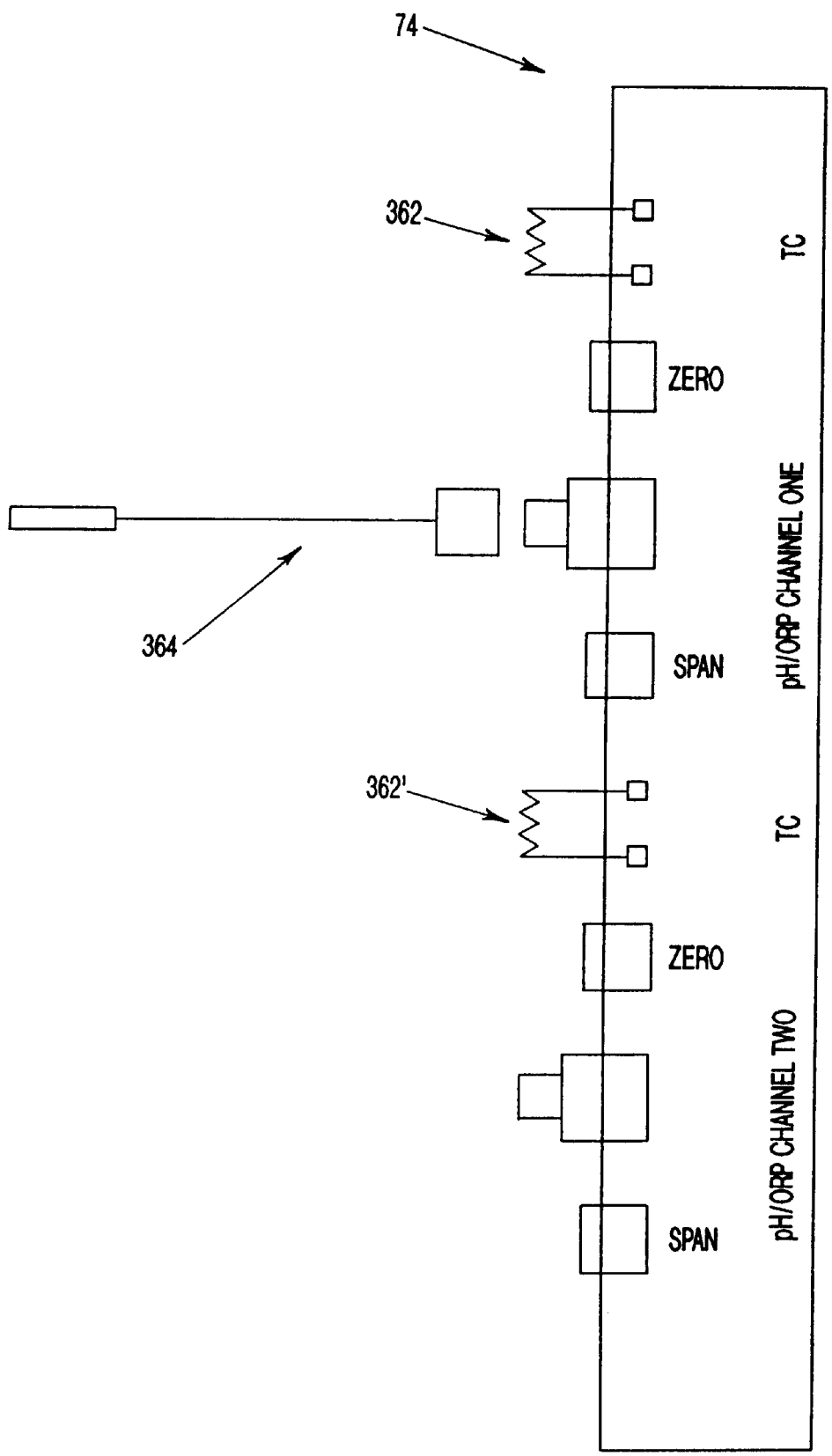
FIG. 10 is a schematic-block diagram of the terminal connections on the pH/ORP input card of the present invention.

PH/ORP input card 74 terminal connections are shown generally in FIG. 10 as a schematic block diagram. PH/ORP input card 74 allows fluid treatment apparatus 100 to monitor two standard pH electrodes, two ORP electrodes, or a combination of the two in the preferred embodiment. PH probes are equipped with 1,000 ohm platinum RTD resistors 362, 362' if temperature compensation is required. In the preferred embodiment, one fluid treatment apparatus 100 will support up to eight pH/ORP input cards 74. Low impedance coaxial cable 364 should be used to connect pH and ORP probes directly to pH/ORP card 74. The input for pH/ORP card 74 is two high impedance analog voltage inputs at plus or minus 1,000 millivolts for pH or ORP electrodes, and two 1,000 ohm platinum RTD resistor temperature sensors. PH/ORP input card 74 is powered by five volts DC or 24 volts DC via the bus connection.

Figure 11:
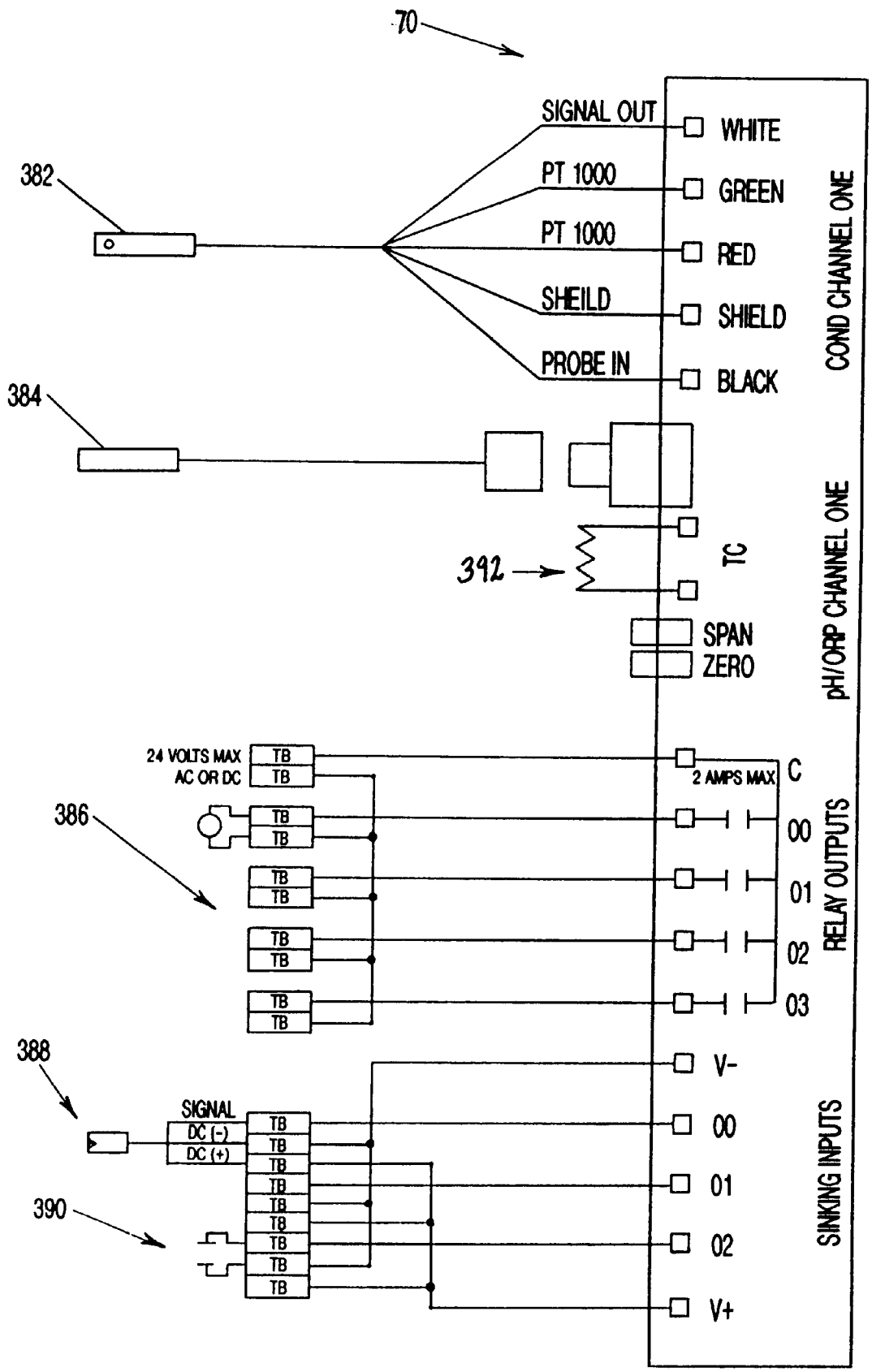
FIG. 11 is a schematic-block diagram of the terminal connections on the water treatment and reverse osmosis combination input card of the present invention.

Water treatment and RO combination input card 70 terminal connections are shown as a schematic block diagram in FIG. 11. Water treatment combination card 70 allows fluid treatment apparatus 100 to monitor one standard conductivity cell, one pH or ORP electrode, and three sinking pulse discrete inputs in the preferred embodiment. Conductivity and pH sensors are equipped with 1,000 ohm platinum RTD resistors for temperature compensation in the preferred embodiment. Water treatment combination card 70 also has four SPST relay outputs. In the preferred embodiment, one fluid treatment apparatus 100 will support up to eight water treatment combination cards 70. Water treatment combination card 70 has one two-electrode conductivity cell input, one high impedance analog voltage input for pH or ORP electrodes, two 1,000 ohm platinum RTD resistor temperature sensors, and three sinking pulse, 12 to 24 volts DC inputs. The output of water treatment combination card 70 contains four SPST relays. Water treatment combination card 70 is powered by five volts DC or 24 volts DC via the bus connection, and 24 volts DC is supplied to Hall effect sensors via the terminal connectors. Sensors 382 should be connected directly to a conductivity card. PH and ORP probes 384 should be connected directly to a pH/ORP card by means of low impedance coaxial cable. Terminal blocks 386 are used to connect fluid treatment apparatus terminals to field wiring. Again, this allows smaller gauge wire to be used on the fluid treatment apparatus terminals. Hall effect flow sensors have three lead connections 388, one for positive DC, one for negative DC, and one for the return signal or sinking pulse. Flow inputs may also be used as discrete inputs 390, such as for hand switches and float switches. The input is high when connected to the low side of the DC supply, sinking input. If pH readings are to be temperature compensated, the pH probe is equipped with a 1,000 ohm platinum RTD resistor 392.

A modem card is also used with fluid treatment apparatus 100 to communicate via standard analog telephone lines.

Fluid treatment apparatus 100 is designed to be panel mounted in various types of electrical enclosures with standard mounting brackets. Although fluid treatment apparatus 100 is shown using card guides 108 to mount the different input/output cards, other configurations for fluid treatment apparatus 100 are available. For example, a separate card cage can be used to store the input/output cards and the input/output cards could alternatively be connected to fluid treatment apparatus 100 with a ribbon cable. However, mounting the various input/output cards in the rear of fluid treatment apparatus 100 provides a compact and simple system which is small enough to be panel-mounted in an electrical enclosure.

Figure 16:
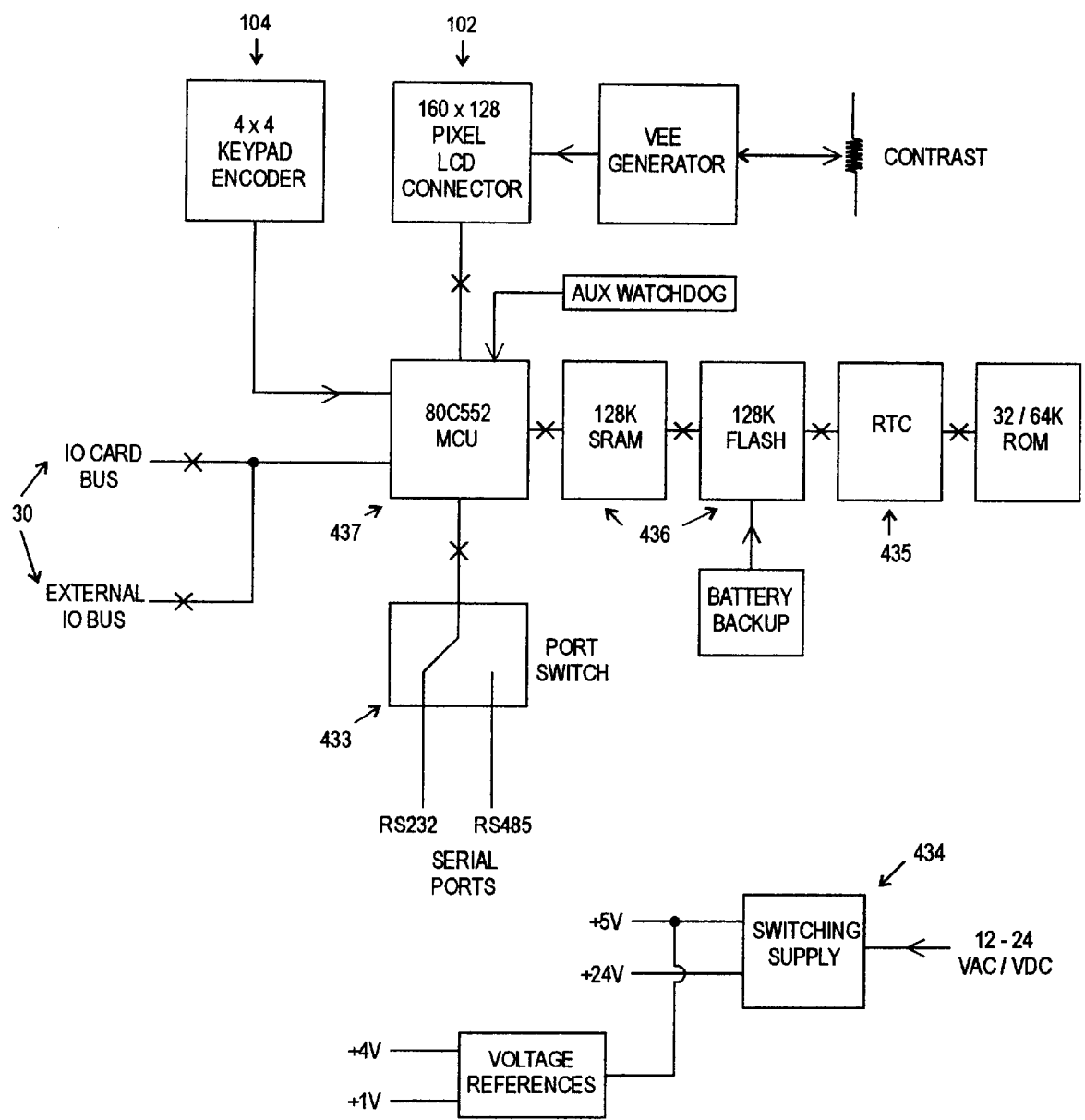
FIG. 16 is an electronic block diagram of the central processing unit of the present invention.

Attention is now turned to FIGS. 16 to 23, where various input/output cards are shown as electrical block diagrams. FIG. 16 shows CPU 124 as an electrical block diagram. Microprocessor 437 is equipped with memory 436 and real time clock 435. Microprocessor 437 is interfaced with keypad 104 and LCD 102. Microprocessor 437 communicates with the various I/O cards by means of I/O card data bus 30. Microprocessor 437 may also communicate with other devices by means of RS 232 or RS 485 serial ports 433. CPU 124 also includes switching power supply 434 which provides 5 volts DC and 24 volts DC to the I/O cards. It also provides reference voltages of 1 volt DC and 4 volts DC.

Figure 17:
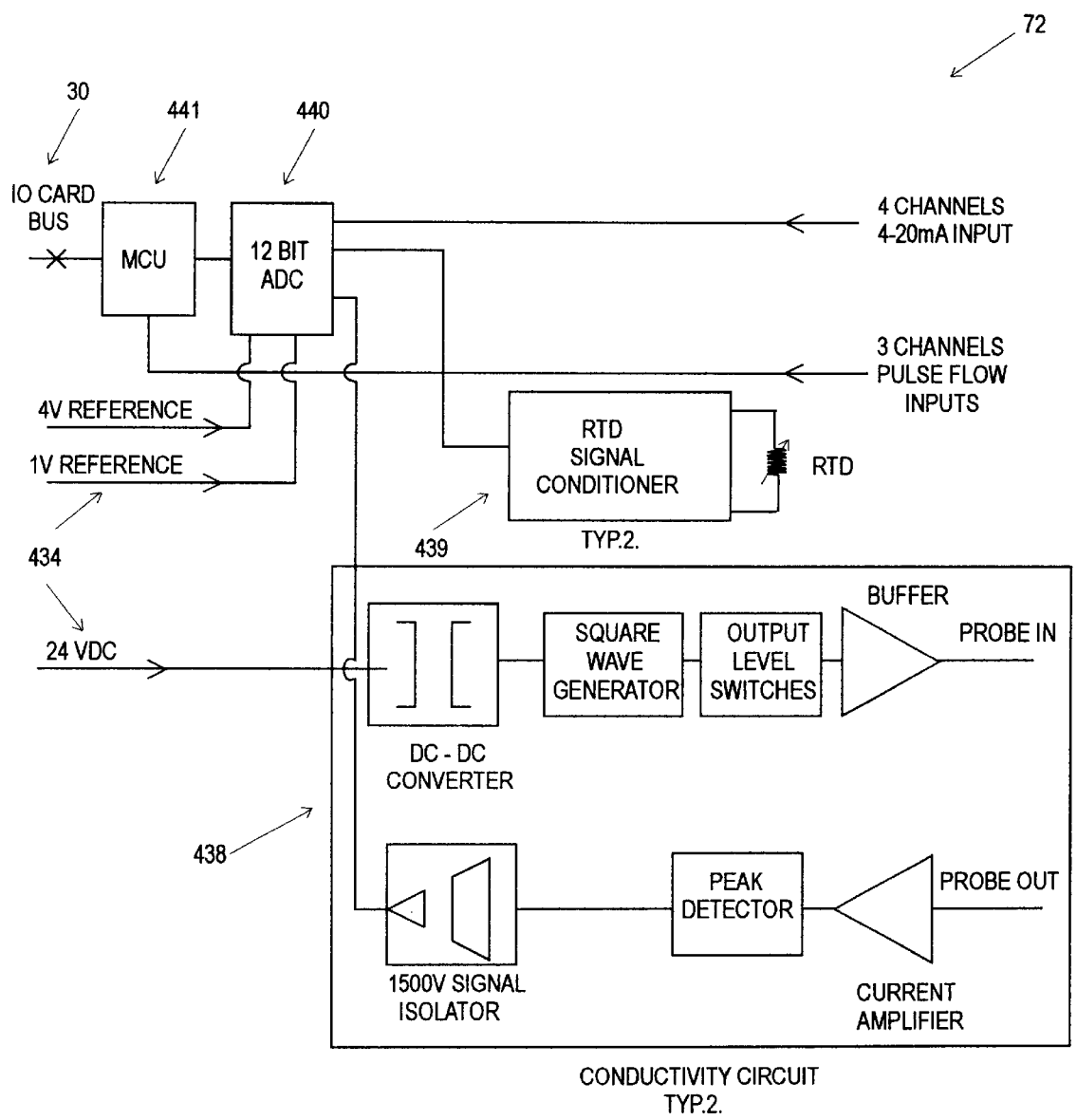
FIG. 17 is an electronic block diagram of the conductivity input card of the present invention.

FIG. 17 shows conductivity card 72 as an electrical block diagram. Eight channel analog to digital converter 440 is connected to the isolated input circuitry for measuring the conductivity across the probe of conductivity measuring circuit 438. Analog to digital converter 440 is also connected to RTD measuring circuit 439 and other analog inputs. Typically, two conductivity measuring circuits 438 and RTD measuring circuits 439 are on one conductivity card. Conductivity measuring circuit 438 receives 24 volt DC power from power supply 434 from CPU 124. Analog to digital converter 440 also receives reference voltages from power supply 434 from CPU 124. Microprocessor 441 in conductivity card 72 receives data from analog to digital converter 440 in addition to external pulse signals from flow sensors and communicates this data to CPU 124 via data bus 30.

Figure 18:
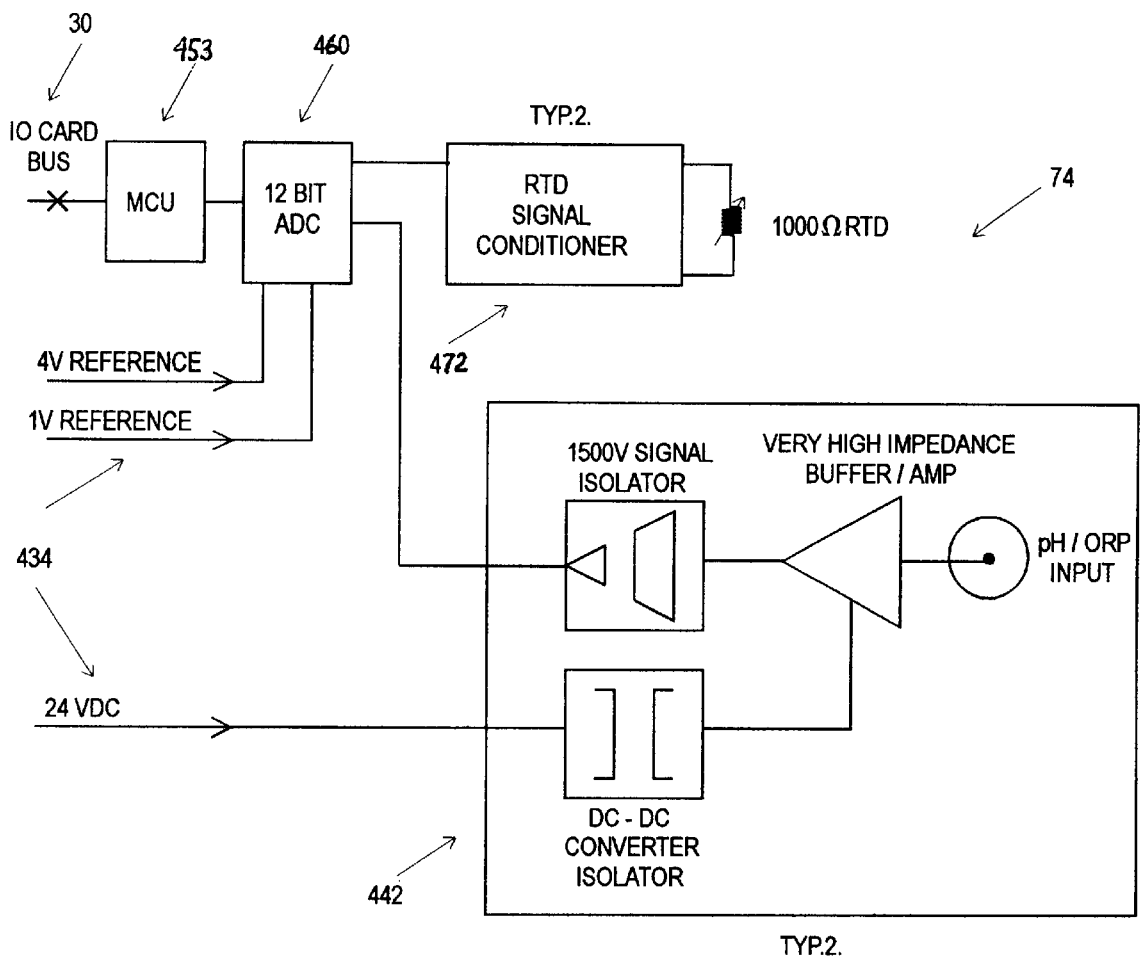
FIG. 18 is an electronic block diagram of the pH/ORP input card of the present invention.

FIG. 18 shows pH/ORP card 74 as an electrical block diagram. Eight channel analog to digital converter 460 is connected to the isolated input circuitry for measuring the pH or ORP from probe of pH/ORP measuring circuit 442. Analog to digital converter 460 is also connected to RTD measuring circuit 472. Typically, two pH/ORP measuring circuits 442 and RTD measuring circuits 472 are on one pH/ORP card. The pH/ORP measuring circuit 442 receives 24 volt DC power from power supply 434 from CPU 124. Analog to digital converter 460 receives reference voltages from power supply 434 from CPU 124. Microprocessor 453 in pH/ORP card 74 receives data from analog to digital converter 460 and communicates this data to CPU 124 via data bus 30.

Figure 19:
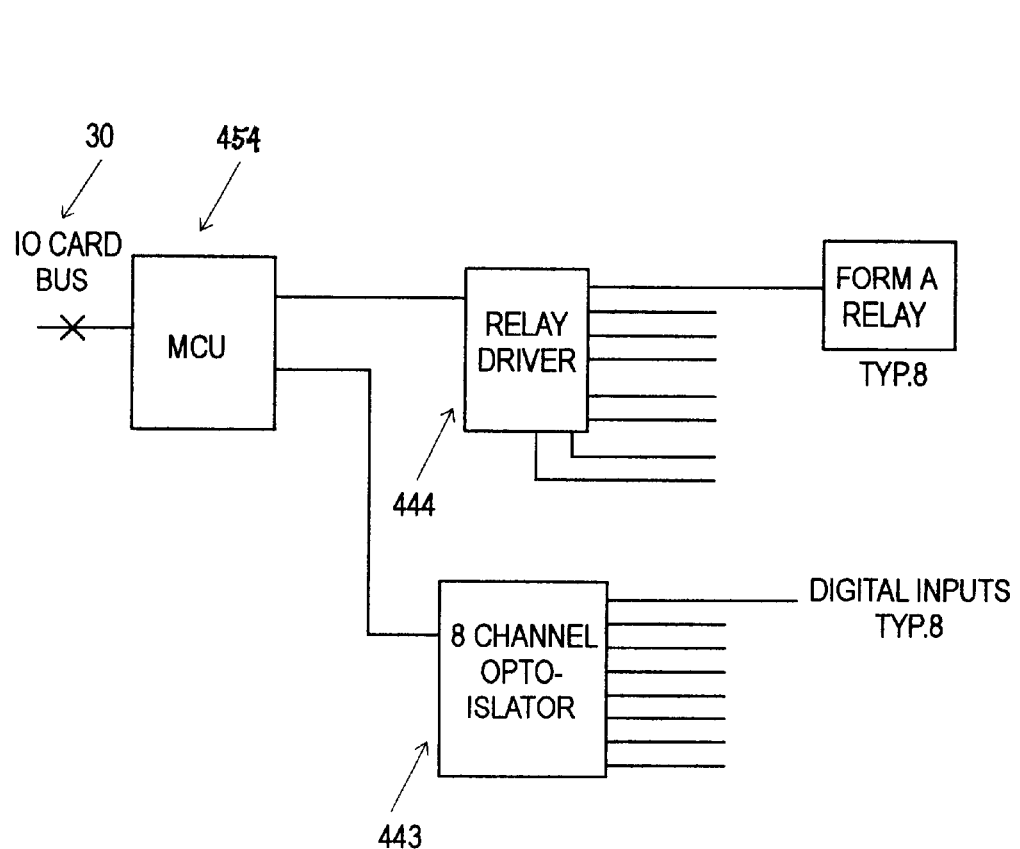
FIG. 19 is an electronic block diagram of the digital input/output card of the present invention.

FIG. 19 shows the digital I/O card 76 as an electrical block diagram. Microprocessor 454 in digital I/O card 76 receives data from opto isolator 443 and communicates this data to CPU 124 via data bus 30. Microprocessor 454 receives data via data bus 30 and communicates this data to relay driver 444 which in turn controls the state of eight SPST relays.

Figure 20:
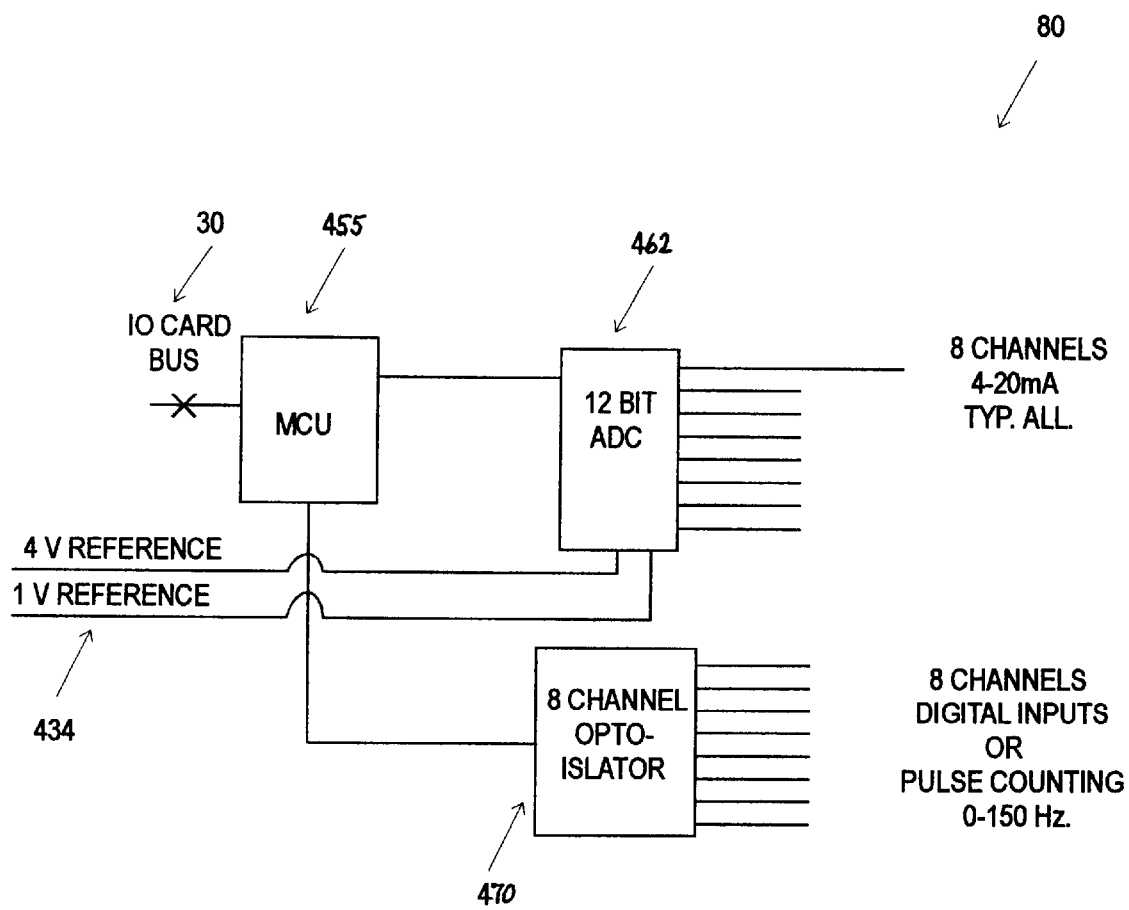
FIG. 20 is an electronic block diagram of the analog/pulse input card of the present invention.

FIG. 20 shows analog/pulse input card 80 as an electrical block diagram. Microprocessor 455 in analog/pulse input card 80 receives discrete or pulse data from opto isolator 470 and communicates this data to CPU 124 via data bus 30. Analog to digital converter 462 is connected to eight analog inputs and sends data to microprocessor 455. Analog to digital converter 462 receives reference voltages from power supply 434 from CPU 124.

Figure 21:
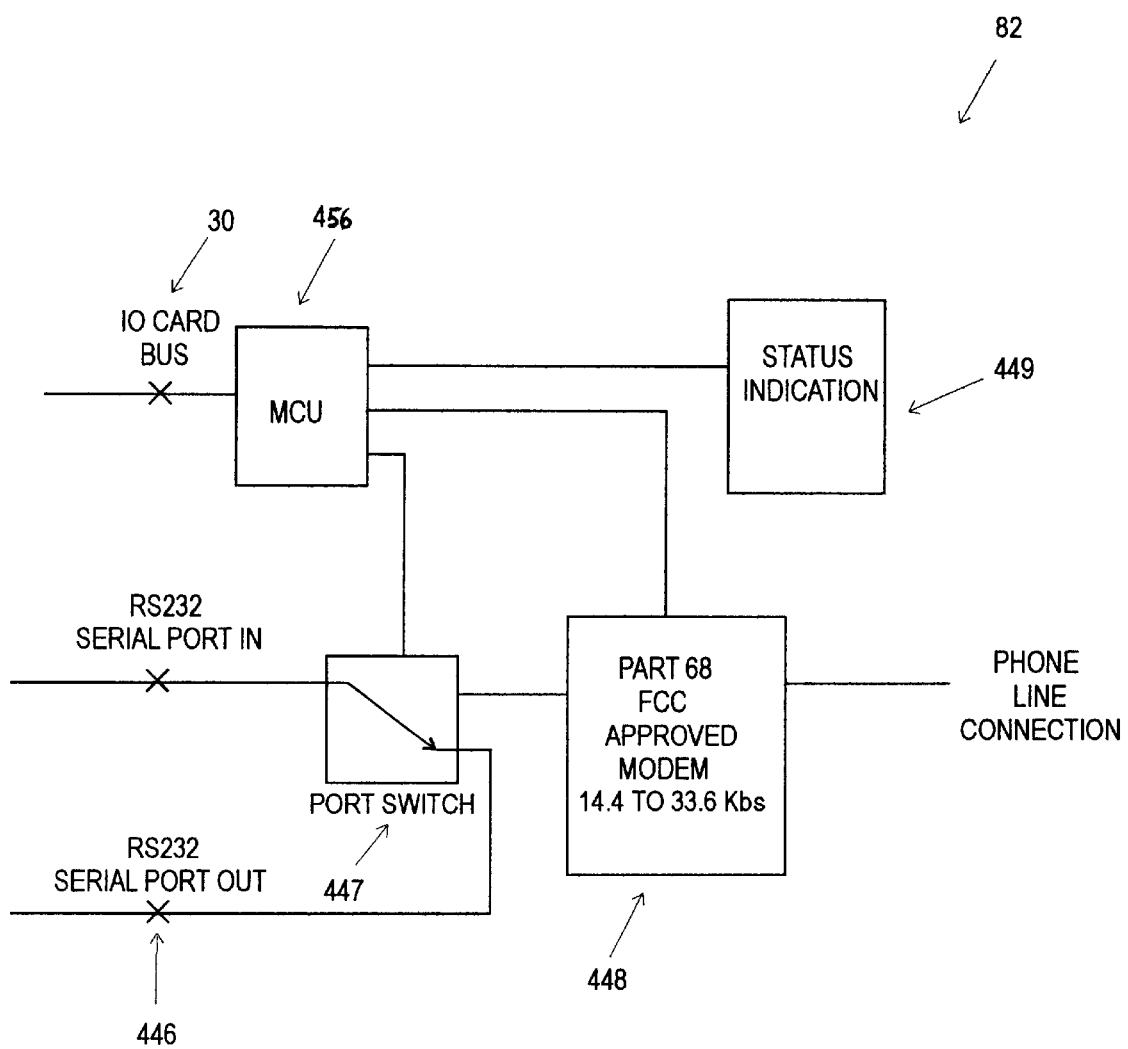
FIG. 21 is an electronic block diagram of the modem card of the present invention.

FIG. 21 shows modem card 82 as an electrical block diagram. Modem module 448 is connected to a standard analog telephone line and sends data to microprocessor 456 which in turn transmits and receives data via an RS 232 serial port 446. Serial port switch 447 allows other devices to communicate with serial port 446 when the modem is not in use. Microprocessor 456 responds to commands received from CPU 124 via data bus 30. Status indicator lights 449 show the status of modem functions.

Figure 22:
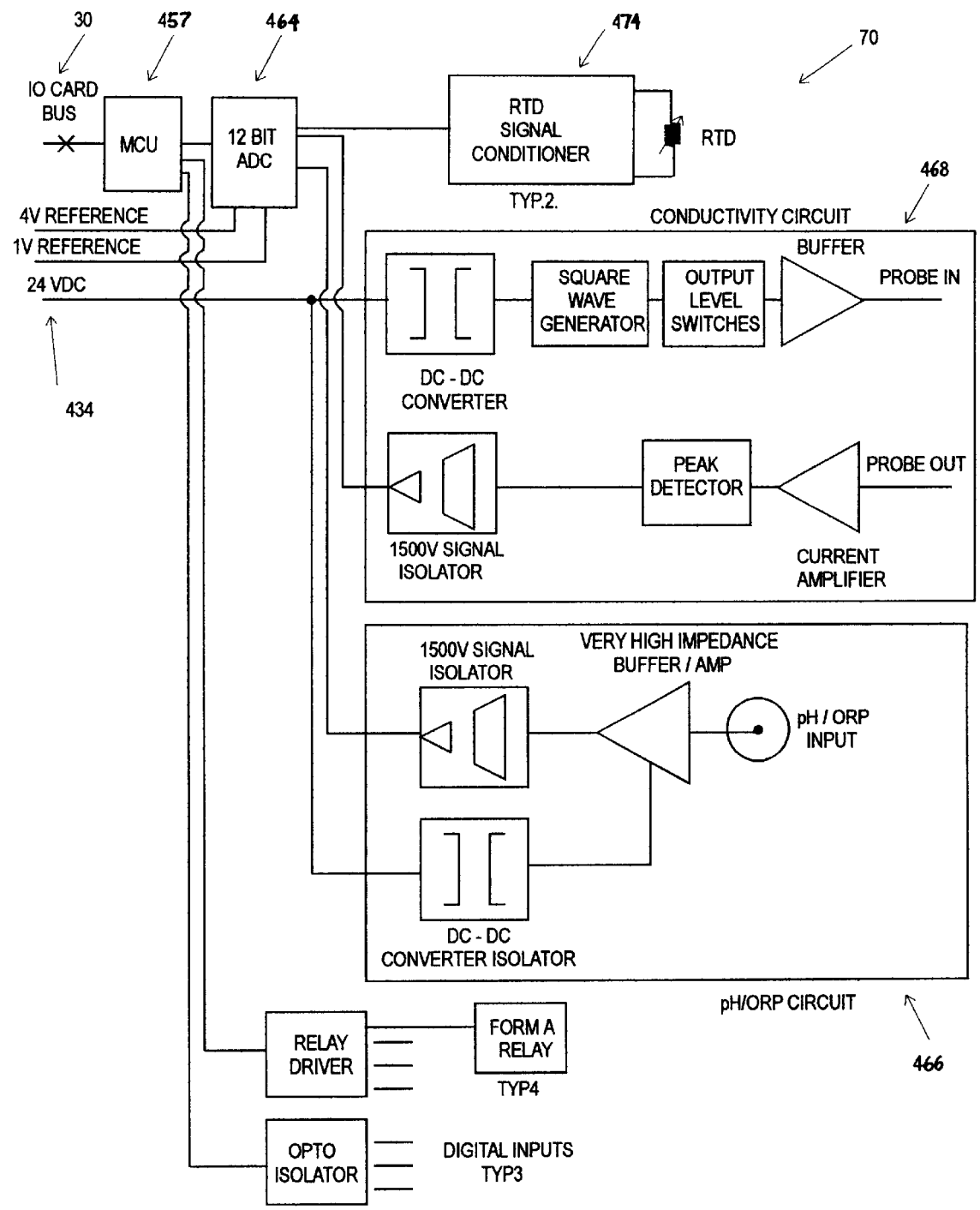
FIG. 22 is an electronic block diagram of the water treatment and reverse osmosis combination input card of the present invention.

FIG. 22 shows water treatment combination card 70 as an electrical block diagram. Eight channel analog to digital converter 464 is connected to the isolated input circuitry for measuring the pH or ORP from the probe of pH/ORP measuring circuit 466. Analog to digital converter 464 is also connected to the isolated input circuitry for measuring the conductivity across the probe of conductivity measuring circuit 468. Analog to digital converter 464 is also connected to two RTD measuring circuits 474. The pH/ORP measuring circuit 466 and conductivity measuring circuit 468 receive 24 volt DC power from power supply 434 from CPU 124. Analog to digital converter 464 receives reference voltages from power supply 434 from CPU 124. Microprocessor 457 in water treatment combination card 70 receives data from analog to digital converter 464 and communicates this data to CPU 124 via data bus 30.

Figure 23:
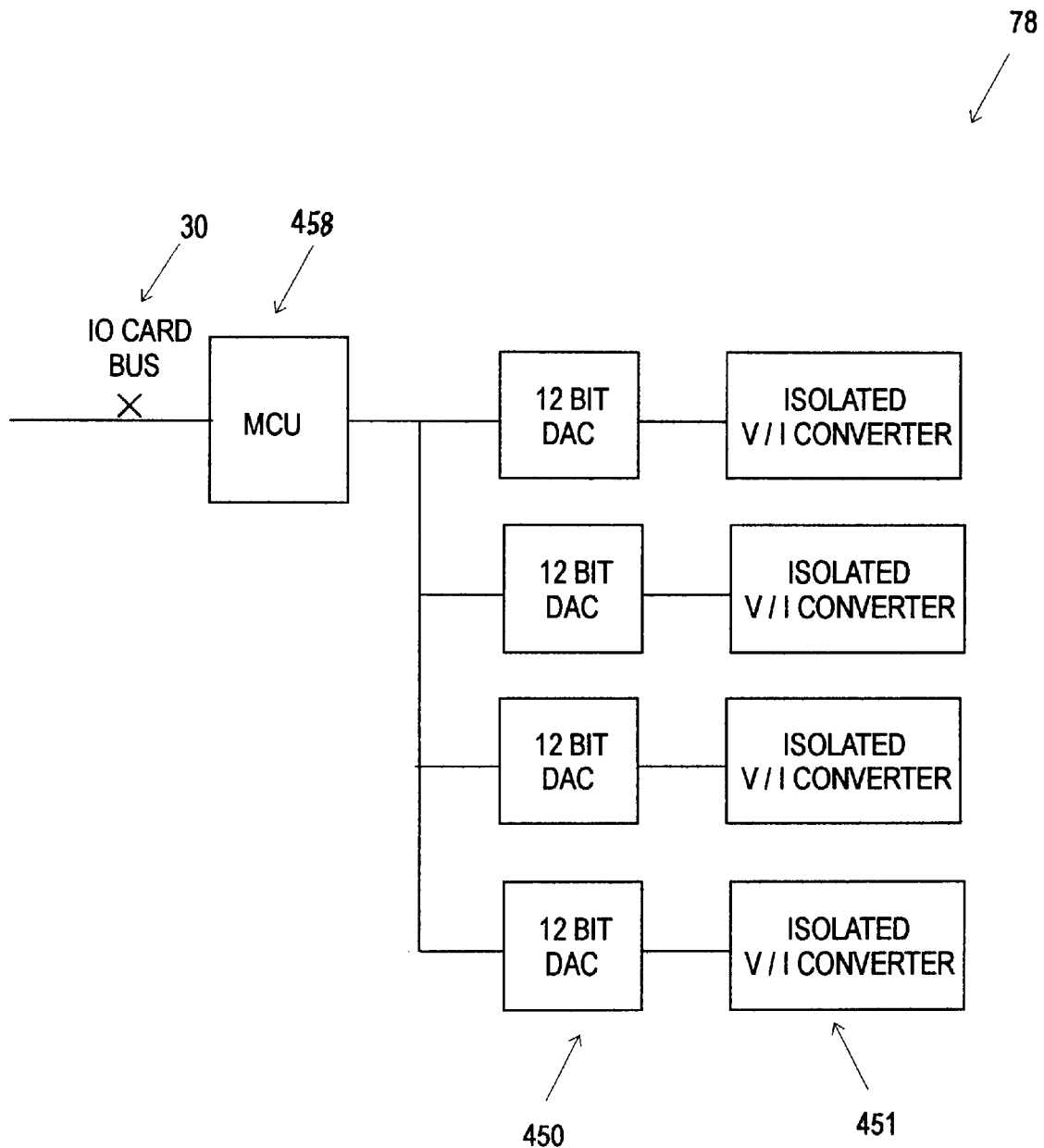
FIG. 23 is an electronic block diagram of the analog output card of the present invention.

FIG. 23 shows analog output card 78 as an electrical block diagram. Microprocessor 458 receives data from CPU 124 via data bus 30. Digital to analog converters 450 convert the data to analog signals. These signals are sent to field devices by means of isolated voltage to current converters 451.

The unique configurations of conductivity card 72, pH/ORP card 74, and water treatment combination card 70—in particular the pH/ORP measuring circuits, conductivity measuring circuits, and RTD measuring circuits—which allow the cards to directly receive analytical parameters has applications not only in the fluid treatment apparatus but in other fields as well. The ability to receive analytical parameters directly into the apparatus is entirely new to the field of computers and monitoring equipment. Variations upon these embodiments for communicating with these particular parameters as well as other types of analytical parameters will be obvious to those skilled in the art.

Industrial Applicability

The invention is further illustrated by the following non-limiting examples.

Figure 12:
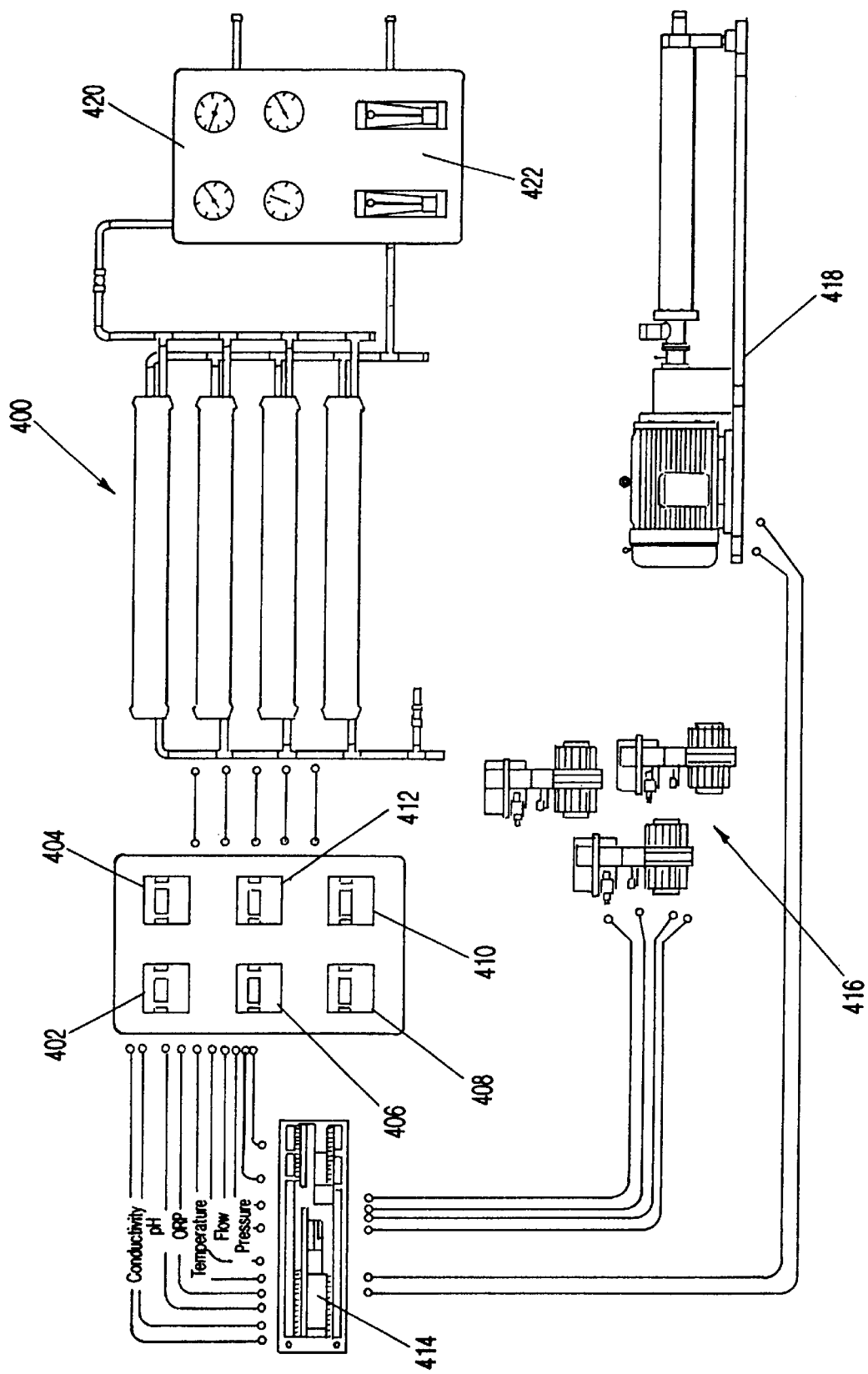
FIG. 12 shows a conventional reverse osmosis system.

FIG. 12 shows a conventional reverse osmosis system. Reverse osmosis vessels are shown generally at 400 and are monitored by pressure gauges 420 and flow meters 422. Various devices are used to monitor the entire system, including conductivity 402, pH 404, ORP 406, flow 408, pressure 410, and temperature 412, which in turn communicate with PLC 414. The PLC then controls motorized valves 416 and high pressure pump 418. With this type of system, many different gauges, meters and discrete devices are required to monitor and control the system.

Figure 13:
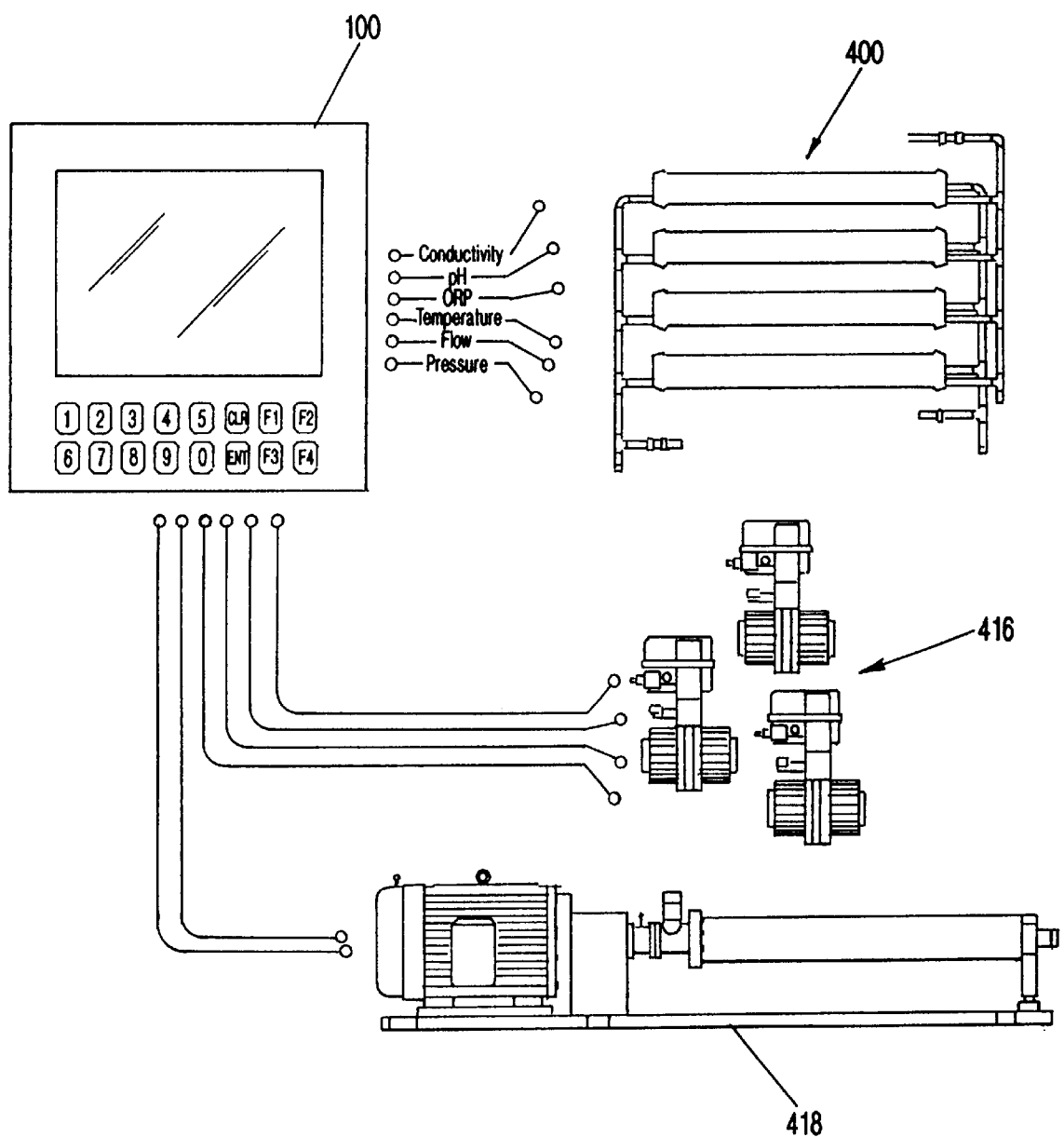
FIG. 13 shows a reverse osmosis system using the present invention.

FIG. 13 shows an improvement on the conventional reverse osmosis system of FIG. 12 by using fluid treatment apparatus 100 of the present invention. Fluid treatment apparatus 100 communicates directly with analytical sensors on reverse osmosis vessels 400 and directly with motorized valves 416. Apparatus 100 also communicates directly with high pressure pump 418. With this configuration, cost is reduced. There are fewer wires, fewer pipes, and no PLC or PLC operator interface is required. Apparatus 100 is able to calculate values such as normalized permeate flow, differential pressure, and salt rejection and can also log data. Fluid treatment apparatus 100 may be connected to another system via the modem communication.

Figure 14:
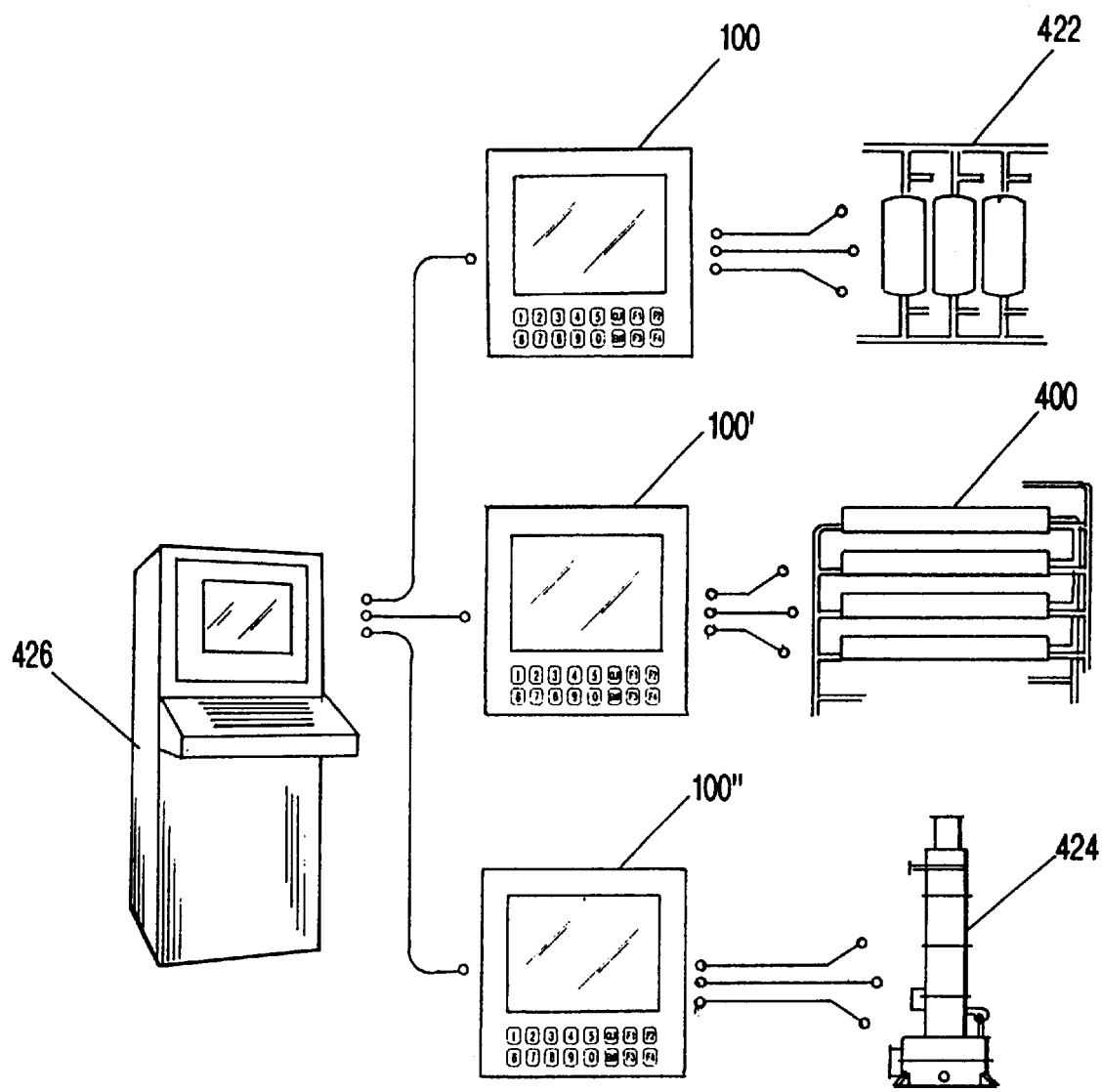
FIG. 14 shows a networking application using the present invention.

FIG. 14 shows another application of fluid treatment apparatus 100 of the present invention. In this example, three apparatuses 100, 100', 100", are networked in a reverse osmosis system. Fluid is pretreated at 422 and communicates directly with apparatus 100. Reverse osmosis vessels 400 communicate directly with apparatus 100' and post-treatment occurs at 422, which also communicates directly with the network via apparatus 100". All three apparatuses 100, 100', and 100" communicate with industrial personal computer 426. With such a networking system, cost is reduced and the entire treatment system is controlled and monitored from a central position. Less wiring is required and the ability to interface with existing control systems is accomplished.

Figure 15:
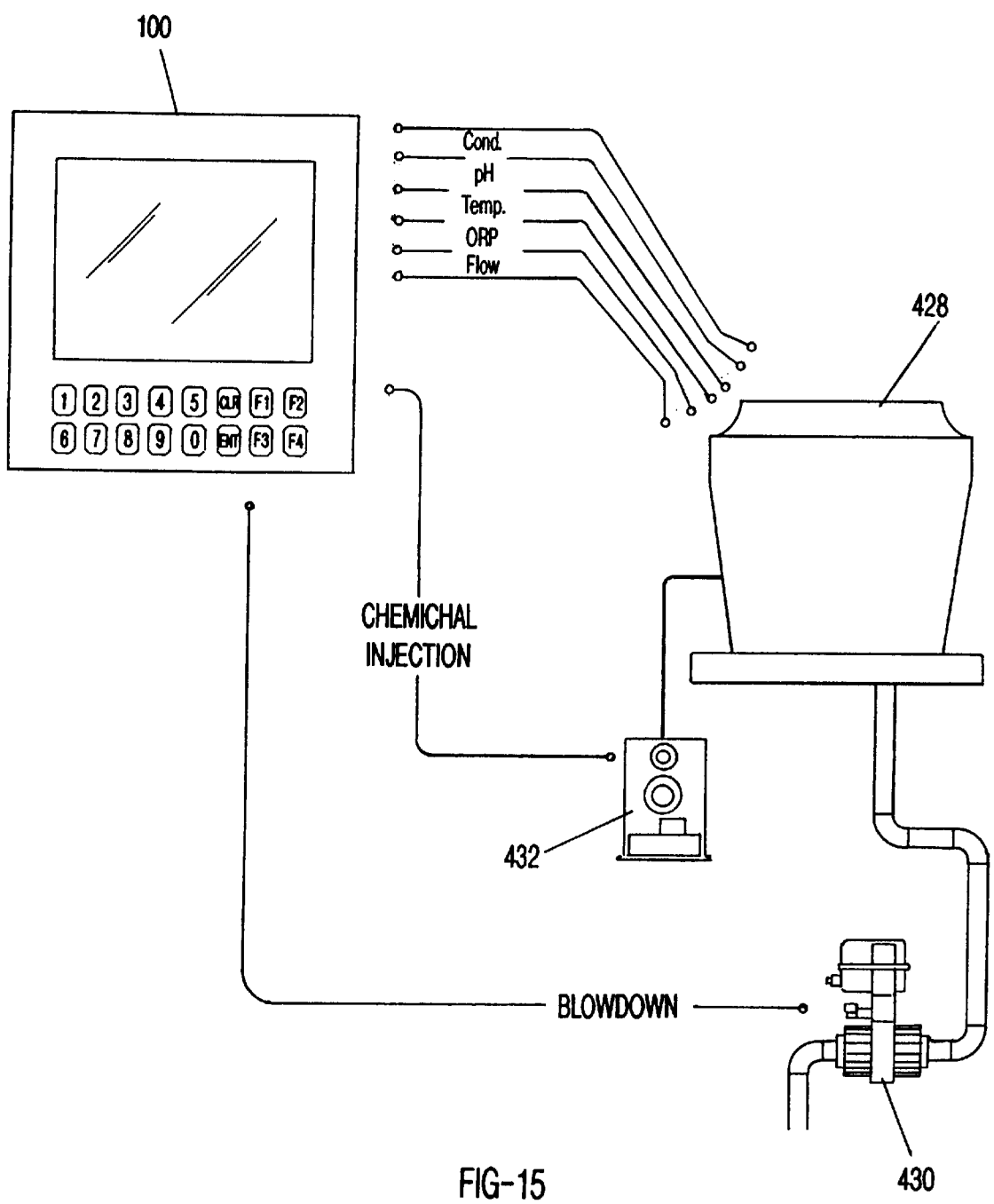
FIG. 15 shows a cooling tower application using the present invention.

FIG. 15 demonstrates yet another application for fluid treatment apparatus 100. In this application, apparatus 100 communicates directly with cooling tower 428, chemical injection pump 432, and valve 430. With this system, chemical injection can be controlled and chemical costs are decreased. This system can also be remotely monitored via the modem connection.

The preceding examples can be repeated with similar success by substituting the generically or specifically described operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An integrated apparatus for monitoring fluid treatment, said apparatus comprising:

a programmable central processing unit for manipulating data and controlling fluid treatment;

at least one interchangeable input/output card for communicating with sensor inputs and said central processing unit;

a data bus for communicating said at least one interchangeable input/output card with said central processing unit;

a keypad for communicating with said central processing unit;

a display for viewing data;

at least one reverse osmosis vessel;

at least one analytical sensor for monitoring said reverse osmosis vessel; and at least one pressure pump in communication with said apparatus, said reverse osmosis vessel and said central processing unit.

2. The apparatus of claim 1 further comprising:

an industrial personal computer for networking a plurality of additional devices;

at least one sensor for monitoring a fluid treatment application and in communication with said personal computer via said additional devices; and at least one control device for controlling said fluid treatment application.

3. The apparatus of claim 1 further comprising:

a cooling tower in communication with said central processing unit;

at least one chemical injection pump in communication with said apparatus; and at least one valve in communication with said central processing unit.

4. An integrated apparatus for monitoring fluid treatment, said apparatus comprising:

a programmable central processing unit for manipulating data and controlling fluid treatment;

at least one interchangeable input/output card for communicating with sensor inputs and said central processing unit;

a data bus for communicating said at least one interchangeable input/output card with said central processing unit;

a keypad for communicating with said central processing unit;

a display for viewing data;

an industrial personal computer for networking a plurality of additional devices;

at least one sensor for monitoring a fluid treatment application and in communication with said personal computer via said additional devices; and at least one control device for controlling said fluid treatment application.

5. An integrated apparatus for monitoring fluid treatment, said apparatus comprising:

a programmable central processing unit for manipulating data and controlling fluid treatment;

at least one interchangeable input/output card for communicating with sensor inputs and said central processing unit;

a data bus for communicating said at least one interchangeable input/output card with said central processing unit;

a keypad for communicating with said central processing unit;

a display for viewing data;

a cooling tower in communication with said central processing unit;

at least one chemical injection pump in communication with said apparatus; and at least one valve in communication with said central processing unit.

* * * * *